US012778433B2

(12) United States Patent
Moon et al.

(10) Patent No.: US 12,778,433 B2
(45) Date of Patent: Nov. 3, 2026

(54) PULSE WAVE GENERATION APPARATUS AND BLOOD PRESSURE CALCULATION SYSTEM INCLUDING THE SAME

(71) Applicant: SAMSUNG DISPLAY CO., LTD., Yongin-si (KR)

(72) Inventors: Gyeong Ub Moon, Yongin-si (KR); Jong Yeop An, Yongin-si (KR); Hyeon Jun Lee, Yongin-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 744 days.

(21) Appl. No.: 18/174,642

(22) Filed: Feb. 26, 2023

(65) Prior Publication Data

US 2024/0032806 A1 Feb. 1, 2024

(30) Foreign Application Priority Data

Jul. 26, 2022 (KR) ........................ 10-2022-0092187

(51) Int. Cl.
*A61B 5/021* (2006.01)
*A61B 5/022* (2006.01)

(52) U.S. Cl.
CPC ...... *A61B 5/02116* (2013.01); *A61B 5/02225* (2013.01); *A61B 2562/0247* (2013.01)

(58) Field of Classification Search
None
See application file for complete search history.

(56) References Cited

U.S. PATENT DOCUMENTS

| | | | | |
|---|---|---|---|---|
| 9,581,876 | B1 * | 2/2017 | Cho | G02F 1/157 |
| 2002/0159491 | A1 * | 10/2002 | Jiang | H01S 5/185 372/45.01 |
| 2006/0104824 | A1 * | 5/2006 | Schnall | A61B 5/02007 417/43 |
| 2010/0324430 | A1 * | 12/2010 | Inoue | A61B 5/02141 600/493 |
| 2012/0302902 | A1 * | 11/2012 | Shin | A61B 5/02225 600/494 |
| 2017/0031491 | A1 * | 2/2017 | Bao | G06F 3/04144 |
| 2019/0380624 | A1 * | 12/2019 | Ota | A61B 5/1116 |
| 2021/0356345 | A1 * | 11/2021 | Li | G02F 1/153 |

FOREIGN PATENT DOCUMENTS

| | | |
|---|---|---|
| KR | 10-2014-0127592 | 11/2014 |
| KR | 10-2020-0107306 | 9/2020 |

* cited by examiner

*Primary Examiner* — Jacqueline Cheng
*Assistant Examiner* — Samuel C Kim
(74) *Attorney, Agent, or Firm* — F. CHAU & ASSOCIATES, LLC

(57) ABSTRACT

A pulse wave generation apparatus includes a pressure sensor sensing an external pressure, an optical adjustment unit configured to change a transmissivity of light, a reflection unit reflecting the light, and a control unit outputting an optical adjustment signal for changing the transmissivity based on a pressure measurement value received from the pressure sensor to the optical adjustment unit.

11 Claims, 29 Drawing Sheets

FF: F1, F2, F3

FF: F1, F2, F3, F4, F5

LCS: LCS1, LCS2

PULSE WAVE GENERATION APPARATUS AND BLOOD PRESSURE CALCULATION SYSTEM INCLUDING THE SAME

CROSS-REFERENCE TO RELATED APPLICATION

This application claims priority under 35 U.S.C. § 119 to Korean Patent Application No. 10-2022-0092187, filed on Jul. 26, 2022 in the Korean Intellectual Property Office, the contents of which are herein incorporated by reference in their entirety.

TECHNICAL FIELD

The present disclosure relates to blood pressure calculation and, more specifically, to a pulse wave generation apparatus and a blood pressure calculation system including the same.

DISCUSSION OF THE RELATED ART

Display devices are devices that display images thereon, and have been used not only in televisions (TVs) and computer monitors, but also in mobile smartphones and tablet personal computers (PCs). Portable display devices are provided with various functions. Examples of such various functions include a camera function, a fingerprint sensor function, and the like.

Recently, as the healthcare industry has attracted the attention of technology companies, methods for more conveniently acquiring biometric information regarding health have been developed. For example, there was an attempt to replace a traditional oscillometric pulse measurement device with an electronic product that is conveniently carried. However, an electronic pulse measurement device requires an independent light source, sensor, and display in itself, and should be separately carried, which is inconvenient.

To test the ability of a device to measure blood pressure, an experiment should be performed on persons. In this case, personal biometric information may be leaked, and it may be difficult to measure a blood pressure in various cases. In addition, the experiment is performed on persons, and thus, there is a large restriction in terms of time and space.

SUMMARY

A pulse wave generation apparatus includes a pressure sensor sensing an external pressure, an optical adjustment unit configured to change a transmissivity of light, a reflection unit reflecting the light, and a control unit outputting an optical adjustment signal for changing the transmissivity based on a pressure measurement value received from the pressure sensor to the optical adjustment unit.

The control unit may detect the pressure measurement value sensed by the pressure sensor as first to N-th pressure sections, and may calculate the optical adjustment signal corresponding to each of the first to N-th pressure sections (where N is a positive integer).

The optical adjustment signal may have a waveform including a peak in each of the first to N-th pressure sections.

The pressure sections may include an M-th pressure section (where M is an integer greater than 1 and smaller than N), and the control unit may calculate amplitudes of first to M-th optical adjustment signals so that the optical adjustment signal sequentially may increase in the first to M-th pressure sections and may calculate amplitudes of M-th to N-th optical adjustment signals so that the optical adjustment signal sequentially decreases in the M-th to N-th pressure sections. It is to be understood that as M is greater than 1 and smaller than N, N can be an integer of 3 or more and M can be an integer of 2 or more.

The optical adjustment unit may include a lower electrode, an upper electrode, and an electrochromic layer interposed between the lower electrode and the upper electrode.

The upper electrode or the lower electrode may receive a voltage according to the optical adjustment signal and may adjust a transmissivity of the electrochromic layer.

The pulse wave generation apparatus may further include a scattering unit disposed on one surface of the optical adjustment unit and scattering light.

The control unit may detect the pressure measurement value as first to N-th pressure sections, and the control unit may calculate the optical adjustment signal including a plurality of waveforms having different amplitudes in at least one of the first to N-th pressure sections.

A first amplitude of a first waveform of the plurality of waveforms may be greater than a second amplitude of a second waveform of the plurality of waveforms.

A blood pressure calculation system includes a pulse wave generation apparatus changing a transmissivity of external light, and a display device sensing an applied pressure and emitting a first light. The pulse wave generation apparatus includes a pressure sensor sensing an applied pressure, an optical adjustment unit configured to change a transmissivity of the first light, a reflection unit reflecting the first light, and a control unit outputting an optical adjustment signal for changing the transmissivity based on a pressure measurement value received from the pressure sensor to the optical adjustment unit. The display device includes a main processor emitting the first light to the optical adjustment unit, sensing a second light transmitted through the optical adjustment unit and reflected by the reflection unit among the first light to generate light sensing data, generating a pulse wave signal based on the light sensing data and the sensed pressure, and analyzing the pulse wave signal to calculate a blood pressure.

The control unit may detect the pressure measurement value sensed by the pressure sensor as first to N-th pressure sections, and may calculate the optical adjustment signal corresponding to each of the first to N-th pressure sections (where N is a positive integer).

The optical adjustment signal may have a waveform including a peak in each of the first to N-th pressure sections.

The pressure sections may include an M-th pressure section (where M is an integer greater than 1 and smaller than N), and the control unit may calculate amplitudes of first to M-th optical adjustment signals so that the optical adjustment signal sequentially increases in the first to M-th pressure sections and may calculate amplitudes of M-th to N-th optical adjustment signals so that the optical adjustment signal sequentially decreases in the M-th to N-th pressure sections.

The main processor may generate a peak detection signal based on peaks of the pulse wave signal and may calculate a peak value of the peak detection signal and a pressure value corresponding to the peak value of the peak detection signal, and may calculate a diastolic blood pressure that is lower than the pressure value, a systolic blood pressure that is higher than the pressure value, and a mean blood pressure according to the pressure value.

The main processor may calculate the mean blood pressure as a pressure value corresponding to the peak value.

The main processor may calculate a first pressure value that is smaller than the pressure value corresponding to 60% to 80% of the peak value in the peak detection signal and a second pressure value that is greater than the pressure value, and may calculate the first pressure value as the diastolic blood pressure and may calculate the second pressure value as the systolic blood pressure.

The control unit may detect the pressure measurement value as first to N-th pressure sections.

The control unit may calculate the optical adjustment signal including a plurality of waveforms having different amplitudes in at least one of the first to N-th pressure sections.

A first amplitude of a first waveform of the plurality of waveforms may be greater than a second amplitude of a second waveform of the plurality of waveforms.

Each cycle of the pulse wave signal may include a plurality of waveforms having different amplitudes, and the equation:

$$RI = \frac{Rp}{Sp}$$

may be satisfied in which RI is a reflected pulse wave ratio, SP is a pulse wave contraction value, RP is a reflected pulse wave value, the pulse wave contraction value is an amplitude of a first waveform of the plurality of waveforms, and the reflected pulse wave value is an amplitude of a second waveform of the plurality of waveforms.

The reflected pulse wave ratio may be the same as a ratio between the first amplitude and the second amplitude.

With a pulse wave generation apparatus according to an embodiment, it is possible to generate pulse wave light similar to light reflected by a blood vessel of a human body by controlling a transmissivity of an optical adjustment unit. Accordingly, it is possible to generate a pulse wave signal and calculate blood pressure information by receiving the pulse wave light.

BRIEF DESCRIPTION OF THE DRAWINGS

The above and other aspects and features of the disclosure will become more apparent by describing in detail embodiments thereof with reference to the attached drawings, in which.

DETAILED DESCRIPTION OF THE EMBODIMENTS

The present invention will now be described more fully hereinafter with reference to the accompanying drawings, in which various embodiments of the invention are shown. This invention may, however, be embodied in different forms and should not necessarily be construed as limited to the embodiments set forth herein. Rather, these embodiments are provided so that this disclosure will be thorough and complete, and will fully convey the scope of the invention to those skilled in the art.

It will also be understood that when a layer is referred to as being "on" another layer or substrate, it can be directly on the other layer or substrate, or intervening layers may also be present. The same reference numbers may indicate the same components throughout the specification and the drawings.

It will be understood that, although the terms "first," "second," etc. may be used herein to describe various elements, these elements should not necessarily be limited by these terms. These terms are only used to distinguish one element from another element. For instance, a first element discussed below could be termed a second element without departing from the teachings of the present invention. Similarly, the second element could also be termed the first element.

Hereinafter, embodiments of the present invention will be described with reference to the attached drawings.

Figure 1:
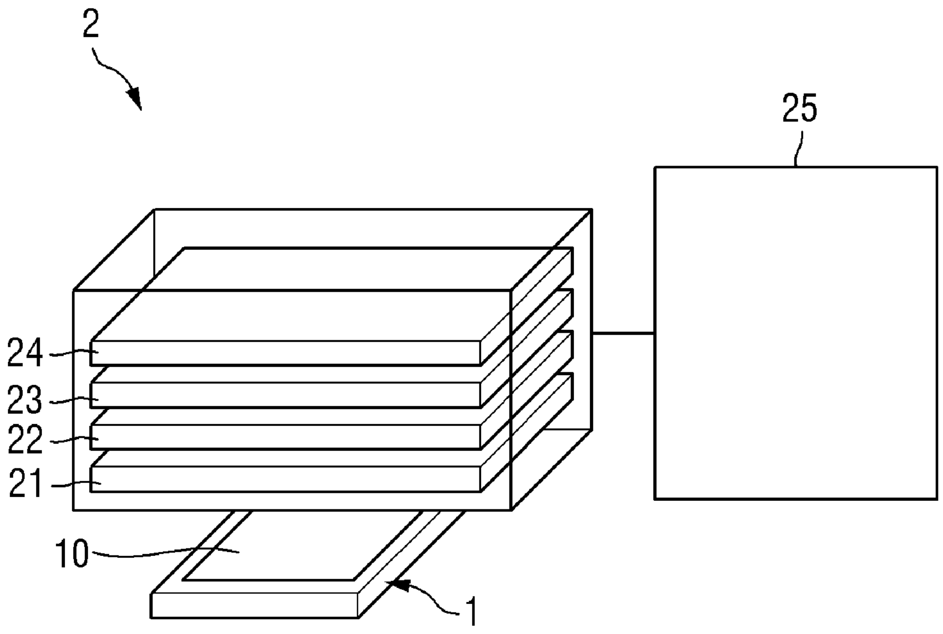
FIG. 1 is a perspective view illustrating a display device and a pulse wave generation apparatus according to an embodiment.
Figure 2:
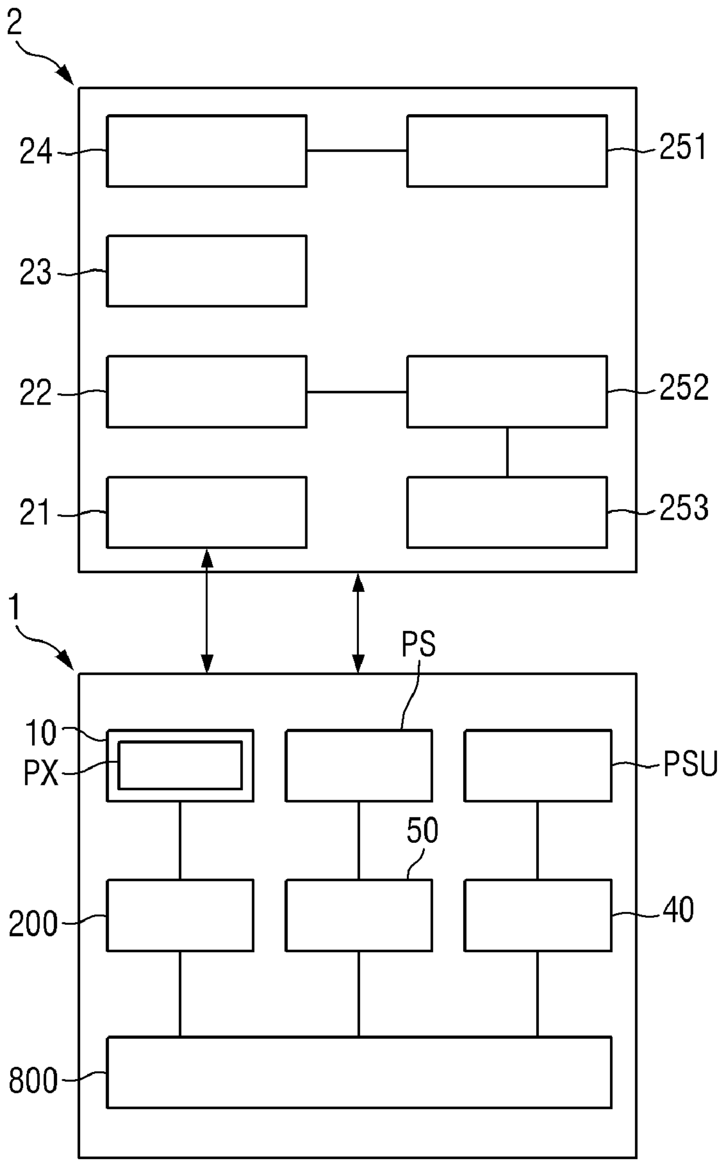
FIG. 2 is a block diagram illustrating the pulse wave generation apparatus according to an embodiment.

FIG. 1 is a perspective view illustrating a display device and a pulse wave generation apparatus according to an embodiment. FIG. 2 is a block diagram illustrating the pulse wave generation apparatus according to an embodiment.

Referring to FIGS. 1 and 2, a blood pressure calculation system, according to an embodiment, includes a display device 1 and a pulse wave generation apparatus 2.

The display device 1 includes a display panel 10, a display driver 200, a pressure sensing unit PSU, and a main processor 800.

The display device 1 calculates a blood pressure using the pulse wave generation apparatus 2. The display device 1 may emit light from the display panel 10 to the pulse wave generation apparatus 2 using an optical method, and sense light reflected from the pulse wave generation apparatus 2. The display device 1 may sense the light reflected from the pulse wave generation apparatus 2 to generate a pulse wave signal PPG (see FIG. 24).

The display panel 10 may include a plurality of pixels PX and may display an image using the plurality of pixels PX. In addition, the display panel 10 may sense the light reflected from the pulse wave generation apparatus 2 through a plurality of photo-sensors PS. The pressure sensing unit PSU may sense a pressure of a human body part such as a finger. Detailed structures of the pixel PX, the photo-sensor PS, and the pressure sensing unit PSU of the display panel 10 will be described in more detail later with reference to the accompanying drawings.

A pulse wave sensing circuit 50 may sense a photocurrent generated by photocharges incident on the plurality of photo-sensors PS of the display panel 10. The pulse wave sensing circuit 50 may recognize a pulse wave of a user based on the photocurrent. In addition, a pressure sensing circuit 40 may sense an electrical signal by a pressure applied to the pressure sensing unit of the display panel 10. The pressure sensing circuit 40 may generate pressure data according to a change in the electrical signal sensed by the pressure sensing unit PSU, and transmit the pressure data to the main processor 800.

The display driver 200 may output signals and voltages for driving the display panel 10. The display driver 200 may supply data voltages to data lines. The display driver 200 may supply a source voltage to a power line and supply gate control signals to a gate driver.

The main processor 800 may control all functions of the display device 1. For example, the main processor 800 may supply digital video data to the display driver 200 so that the display panel 10 displays the image. In addition, the main processor 800 may calculate a pulse wave signal PPG reflecting a blood change depending on a heartbeat according to an optical signal input from the pulse wave sensing circuit 50. In addition, the main processor 800 may calculate a touch pressure of the user according to the electrical signal input from the pressure sensing circuit 40. In addition, the main processor 800 may calculate a blood pressure of the user based on the pulse wave signal PPG (see FIG. 24) and a pressure signal.

The pulse wave generation apparatus 2 may receive the light emitted from the display device 1 and generate light similar to light reflected from a blood vessel of the human body. The pulse wave generation apparatus 2 may adjust an intensity of incident light and output the light of which the intensity is adjusted so that the display device 1 generates the pulse wave signal PPG (see FIG. 24).

The pulse wave generation apparatus 2 includes a scattering unit 21, an optical adjustment unit 22, a reflection unit 23, a pressure sensor 24, and a control unit 25.

The scattering unit 21 may scatter externally incident light or light generated from the pixels PX of the display device 1 (hereinafter, referred to as incident light). The scattering unit 21 may be formed of a polymer resin or a plurality of scatterers mixed with the polymer resin. For example, the scattering unit 21 may include any one of silicon, polycarbonate, polyethylene, a methacrylic resin, polycarbonate, and polyethylene terephthalate. The scattering unit 21 may be manufactured in the form of a film and be attached to one surface of the optical adjustment unit 22 or may be formed integrally with the pulse wave generation apparatus 2.

The optical adjustment unit 22 may be disposed on the scattering unit 21. The optical adjustment unit 22 may have a light transmissivity that is changed. The optical adjustment unit 22 may include an electrochromic layer having electrochromism. For example, when a voltage is applied to both ends of the optical adjustment unit 22, a color may change reversibly. For example, a transmissivity of the optical adjustment unit 22 may increase as the voltage applied to both ends of the optical adjustment unit 22 increases. However, the disclosure is not necessarily limited thereto, and a transmissivity of the optical adjustment unit 22 may also decrease as the voltage applied to both ends of the optical adjustment unit 22 increases.

However, the disclosure is not necessarily limited thereto, and the optical adjustment unit 22 may include a variable shutter, a polarizing member, an energized liquid crystal, and the like, to change a transmissivity of light incident from the outside.

The reflection unit 23 may be disposed on the optical adjustment unit 22. The reflection unit 23 serves to reflect light transmitted through the optical adjustment unit 22 so that the light transmitted through the optical adjustment unit 22 is reflected to the display device 1 again. The reflection unit 23 may include a material capable of reflecting the light. In addition, the pressure sensor 24 may sense a pressure varying according to a touch pressure of the user. The pressure sensor 24 may output pressure measurement values to the control unit 25. The pressure sensor 24 may be formed in a transparent sheet type in which a plurality of transparent electrodes are arranged in vertical and horizontal directions.

The control unit 25 includes a sensing unit 251, a calculation unit 252, and a memory 253.

The sensing unit 251 may receive the pressure measurement value from the pressure sensor 24. The sensing unit 251 may receive a pressure measurement value over time and generate a pressure signal. The sensing unit 251 may output the pressure signal to the calculation unit.

Figure 3:
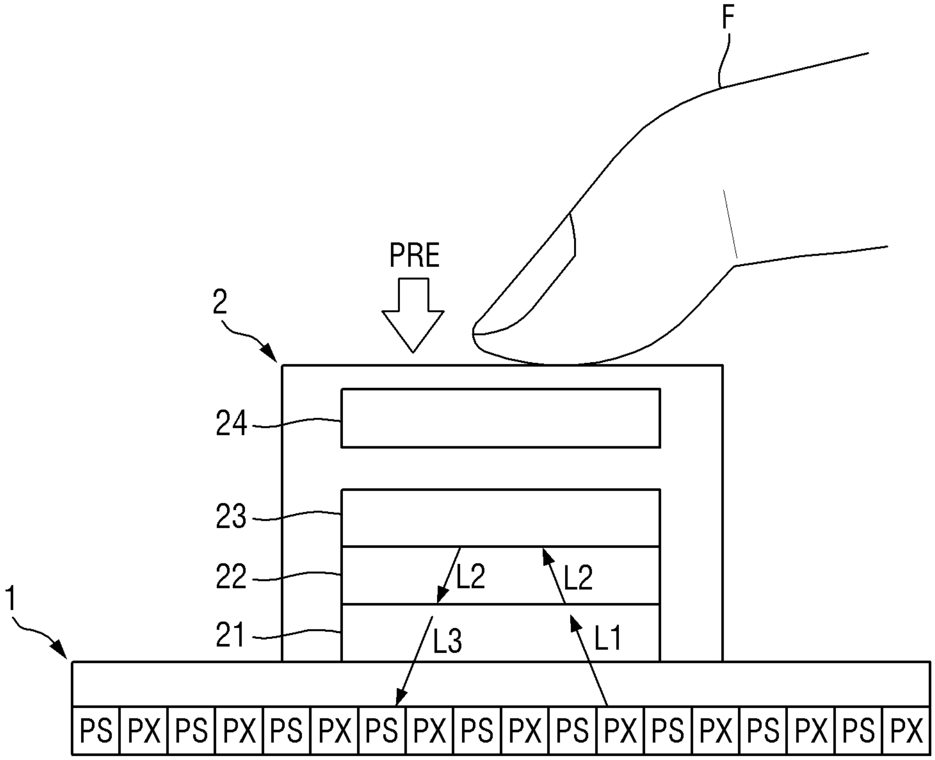
FIG. 3 is a cross-sectional view illustrating a pulse wave test method of the pulse wave generation apparatus according to an embodiment.

The calculation unit 252 may control a function for generating pulse wave light L2 and L3 (see FIG. 3). For example, the calculation unit 252 may receive the pressure signal from the sensing unit 251. In addition, the calculation unit 252 may receive data of an optical adjustment signal LCS (see FIG. 10). The calculation unit 252 may generate the optical adjustment signal based on the received pressure signal and data of the optical adjustment signal LCS (see FIG. 10). The optical adjustment signal LCS (see FIG. 10) refers to a signal for controlling the optical adjustment unit 22 so as to generate the pulse wave light L2 and L3 (see FIG. 3) similar to the light reflected from the blood vessel of the human body. In this case, different pulse wave light L2 and L3 (see FIG. 3) should be generated according to a human health state and mental state or health of the blood vessel and the heart. Accordingly, the calculation unit 252 may generate the optical adjustment signal LCS (see FIG. 10) for generating various pulse wave light L2 and L3 (see FIG. 3). The calculation unit 252 may output the generated optical adjustment signal LCS (see FIG. 10) to the optical adjustment unit 22.

The memory 253 may store data for generating the pulse wave light of the pulse wave generation apparatus 2. The memory 253 may store data that allows the pulse wave generation apparatus 2 to generate the pulse wave light L2 and L3 (see FIG. 3) similar to the light reflected from the blood vessel of the human body. For example, the memory 253 may store the data of the optical adjustment signal LCS (see FIG. 10) for generating the pulse wave light L2 and L3 (see FIG. 3). The memory 253 may store data of various optical adjustment signals LCS (see FIG. 10) for generating the pulse wave light L2 and L3 (see FIG. 3) according to the human health state and mental state or the health of the blood vessel and the heart. In this case, the memory 253 may store data on a peak value or an amplitude for each width or each cycle of the optical adjustment signal LCS (see FIG. 10). The memory 253 may output the stored data to the calculation unit 252.

Accordingly, the pulse wave generation apparatus 2 may generate the pulse wave light L2 and L3 (see FIG. 3), and the display device 1 may sense the pulse wave light L2 and L3 (see FIG. 3) to calculate a blood pressure.

Figure 4:
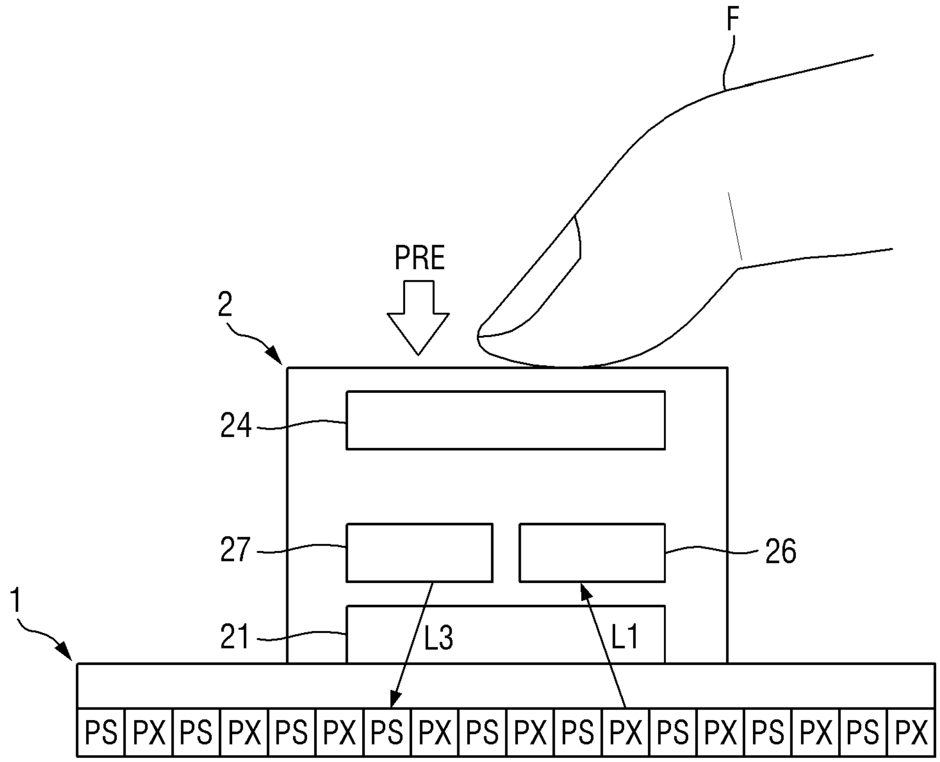
FIGS. 4 and 5 are cross-sectional views illustrating pulse wave test methods of the pulse wave generation apparatus according to other embodiments.
Figure 5:
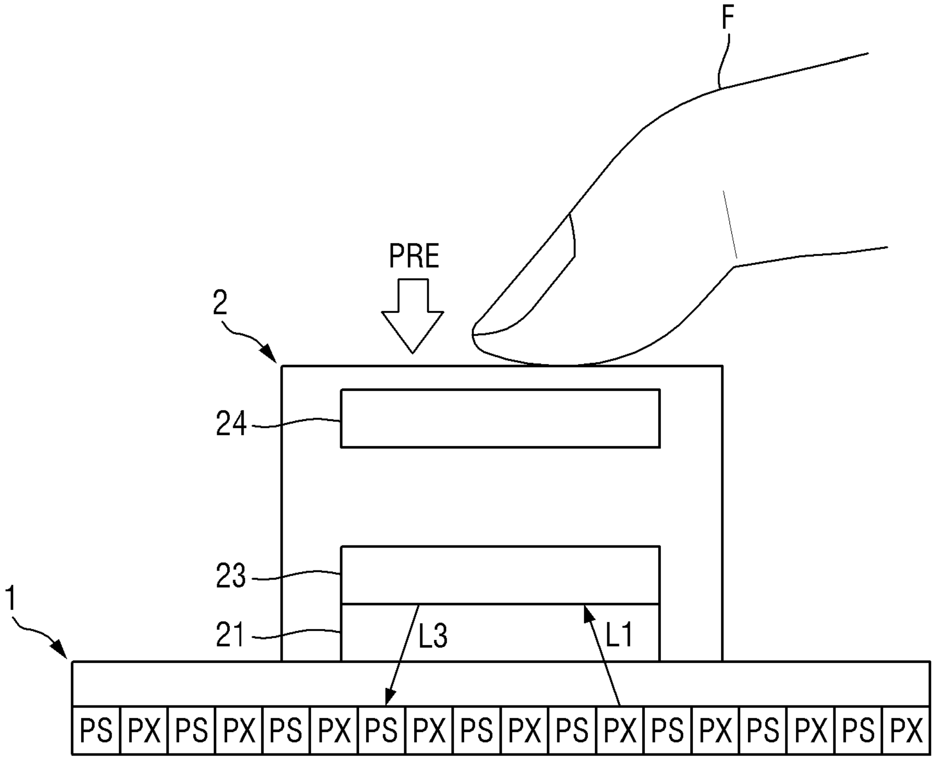

FIG. 3 is a cross-sectional view illustrating a pulse wave test method of the pulse wave generation apparatus 2 according to an embodiment. FIGS. 4 and 5 are cross-sectional views illustrating pulse wave test methods of the pulse wave generation apparatus 2 according to other embodiments.

Referring to FIG. 3, when a finger F of the user comes into contact with an upper surface of the pulse wave generation apparatus 2, the pressure sensor 24 may measure a pressure PRE applied by the user. Accordingly, the control unit 25 may calculate pressure data over time. For example, in a process in which the user brings the finger F into contact with the upper surface of the pulse wave generation apparatus 2, a pressure sensed by the pressure sensor 24 may gradually increase over time to reach a maximum value. When the pressure (i.e., a contact pressure) increases, a blood vessel may be constricted, such that a blood flow rate may be decreased or become 0.

Figure 24:
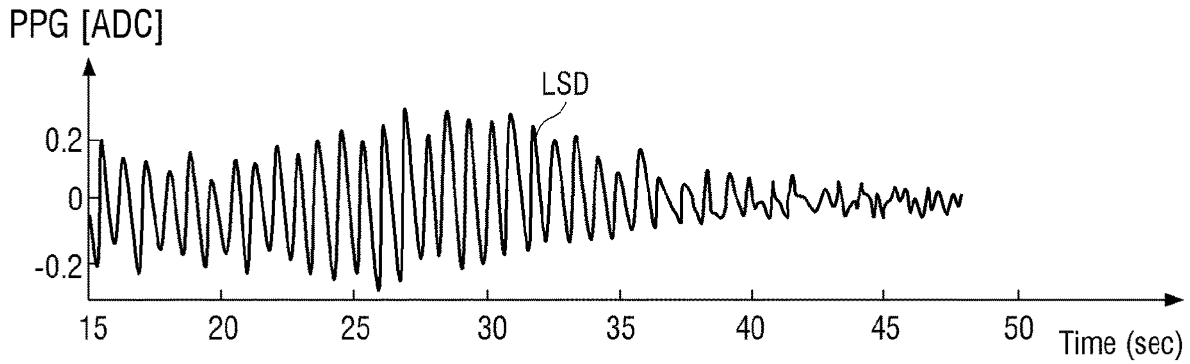
FIG. 24 is a graph illustrating a pulse wave signal over time.

The display device 1 may generate the pulse wave signal PPG (see FIG. 24), and calculate a blood pressure based on the pulse wave signal PPG. A method in which the display device 1 comes into contact with the human body to generate the pulse wave signal PPG (see FIG. 24) will be described. The blood vessel of the human body is exposed to light from the pixel PX. When a peripheral blood vessel is exposed to light emitted from the pixel, the light may be absorbed by a peripheral tissue. Since an absorbance is dependent on a hematocrit and a blood volume, absorbance at a corresponding point in time may be estimated through light reception data of an amount of light sensed by the photo-sensor PS, and accordingly, as illustrated in FIG. 24, the pulse wave signal PPG value over time may be generated.

Thus, in order for the display device 1 to generate the pulse wave signal PPG (see FIG. 24), the pixel PX exposes the blood vessel or the like of the human body to the light, and the photo-sensor PS senses light reflected from the blood vessel or the like. The photo-sensor PS may generate the pulse wave signal PPG (see FIG. 24) by analyzing the sensed light.

Accordingly, the pulse wave generation apparatus 2 may generate the light similar to the light reflected from the blood vessel of the human body. For example, an incident light L1 emitted from the pixel PX of the display device 1 to the pulse wave generation apparatus 2 may be transmitted through the optical adjustment unit 22 of the pulse wave generation apparatus 2. In this case, the pulse wave generation apparatus 2 may generate a first pulse wave light L2 of which an intensity is adjusted by the transmission of the light through the optical adjustment unit 22. In addition, the first pulse wave light L2 may be reflected by the reflection unit 23 and may be retransmitted through the optical adjustment unit 22. The pulse wave generation apparatus 2 may generate a second pulse wave light L3 of which an intensity is adjusted by the re-transmission of the light through the optical adjustment unit 22.

Thus, in the blood pressure calculation system, the pulse wave generation apparatus 2 may be exposed to the light emitted from the pixel PX of the display device 1, and the pulse wave generation apparatus 2 may adjust the intensity of the light to generate the second pulse wave light L3. Accordingly, the photo-sensor PS of the display device 1 may sense the second pulse wave light L3 to generate the pulse wave signal PPG (see FIG. 24), and calculate a blood pressure based on the pulse wave signal PPG.

However, the disclosure is not necessarily limited thereto, and the second pulse wave light L3 may also be generated as is shown in FIG. 4. For example, the arrangement of FIG. 4 is different from the arrangement of FIG. 3 in that the reflection unit 23 and the optical adjustment unit 22 are removed and a pulse wave light emitting unit 27 and a pulse wave light receiving unit 26 are disposed.

Referring to FIG. 4, the pulse wave generation apparatus 2 includes the pulse wave light emitting unit 27 and the pulse wave light receiving unit 26. The pulse wave light receiving unit 26 and the pulse wave light emitting unit 27 of FIG. 4 may perform the same roles as the optical adjustment unit 22 and the reflection unit 23 of the arrangement of FIG. 3. For example, the pulse wave light receiving unit 26 may receive an incident light L1 emitted from the pixel PX of the display device 1. The pulse wave light receiving unit 26 may output data of the received incident light L1 to the control unit 25. In addition, the control unit 25 may adjust an intensity of the incident light L1 based on the received data of the incident light L1. In this case, the intensity of the incident light L1 may be adjusted to be similar to an intensity of the light reflected by the blood vessel of the human body. Accordingly, the pulse wave light emitting unit 27 may emit the second pulse wave light L3 having the intensity adjusted by the control unit 25. For example, in the blood pressure calculation system, according to the embodiment, the photo-sensor PS of the display device 1 may sense the second pulse wave light L3 to generate the pulse wave signal PPG (see FIG. 24), and calculate the blood pressure based on the pulse wave signal PPG.

Alternatively, the second pulse wave light L3 may also be generated as shown in FIG. 5. The arrangement of FIG. 5 is substantially the same as the arrangement of FIG. 3 except that the reflection unit 23 and the optical adjustment unit 22 are formed integrally with each other.

Referring to FIG. 5, the reflection unit 23 and the optical adjustment unit 22 may be formed integrally with each other. Accordingly, the incident light L1 emitted from the pixel PX of the display device 1 may be transmitted through the optical adjustment unit 22 and may be reflected inside the optical adjustment unit 22. Accordingly, the photo-sensor of the display device 1 may sense the reflected second pulse wave light L3. A method in which the pulse wave generation apparatus 2 generates the second pulse wave light L3 and a method in which the display device 1 calculates the blood pressure will be described later.

Figure 6:
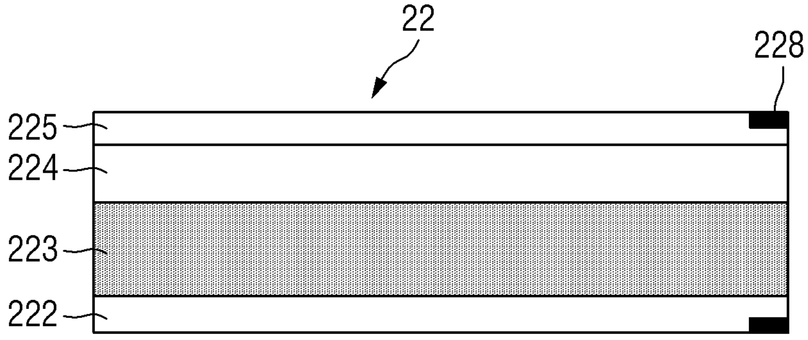
FIG. 6 is a cross-sectional view illustrating an optical adjustment unit according to an embodiment.

FIG. 6 is a cross-sectional view illustrating an optical adjustment unit according to an embodiment.

Referring to FIG. 6, the optical adjustment unit 22 includes a lower electrode 222, an electrochromic layer 223, an electrolyte layer 224, an upper electrode 225, and supply electrodes 228.

The lower electrode 222 may be disposed on one surface of the electrochromic layer 223. In addition, the lower electrode 222 may also be disposed on the other surface of the electrochromic layer 223. The upper electrode 225 may be disposed on the other surface of the electrochromic layer 223 so as to face the lower electrode 222. In addition, the upper electrode 225 may also be disposed on one surface of the electrochromic layer 223 so as to face the lower electrode 222.

Each of the lower electrode 222 and the upper electrode 225 may be formed as an indium tin oxide (ITO) layer (hereinafter, referred to as an ITO layer). The ITO layer may include an ITO film or ITO glass form. In addition, the ITO layer may be implemented by replacing ITO with a replaceable silver nanowire, a copper mesh, a silver mesh, a silver salt, and a silver nanoparticle.

The electrochromic layer 223 may be interposed between the lower electrode 222 and the upper electrode 225. The electrochromic layer 223 may have a light transmissivity that is changed according to a supply voltage. For example, when a voltage is applied to both ends of the electrochromic layer 223, a color thereof may change. For example, a transmissivity of the electrochromic layer 223 may increase as the voltage applied to both ends of the electrochromic layer 223 increases. However, the disclosure is not necessarily limited thereto, and a transmissivity of the electrochromic layer 223 may also decrease as the voltage applied to both ends of the electrochromic layer 223 increases. For example, the transmissivity of the electrochromic layer 223 may be changed. In addition, the electrolyte layer 224 may be disposed on the electrochromic layer 223.

The supply electrodes 228 may be connected to the upper electrode 225 and the lower electrode 222, respectively, and may receive supply voltages input thereto. The supply electrodes 228 may be implemented as transparent electrodes. The supply electrodes 228 may input the supply voltages to the lower electrode 222 and the upper electrode 225, respectively. It may be easily understood by one of ordinary skill in the art that position (e.g., the lower right end of the lower electrode 222 and the upper right end of the upper electrode 225) of the respective supply electrodes 228 may be changed according to performance or a structure of the optical adjustment unit 22.

Figure 7:
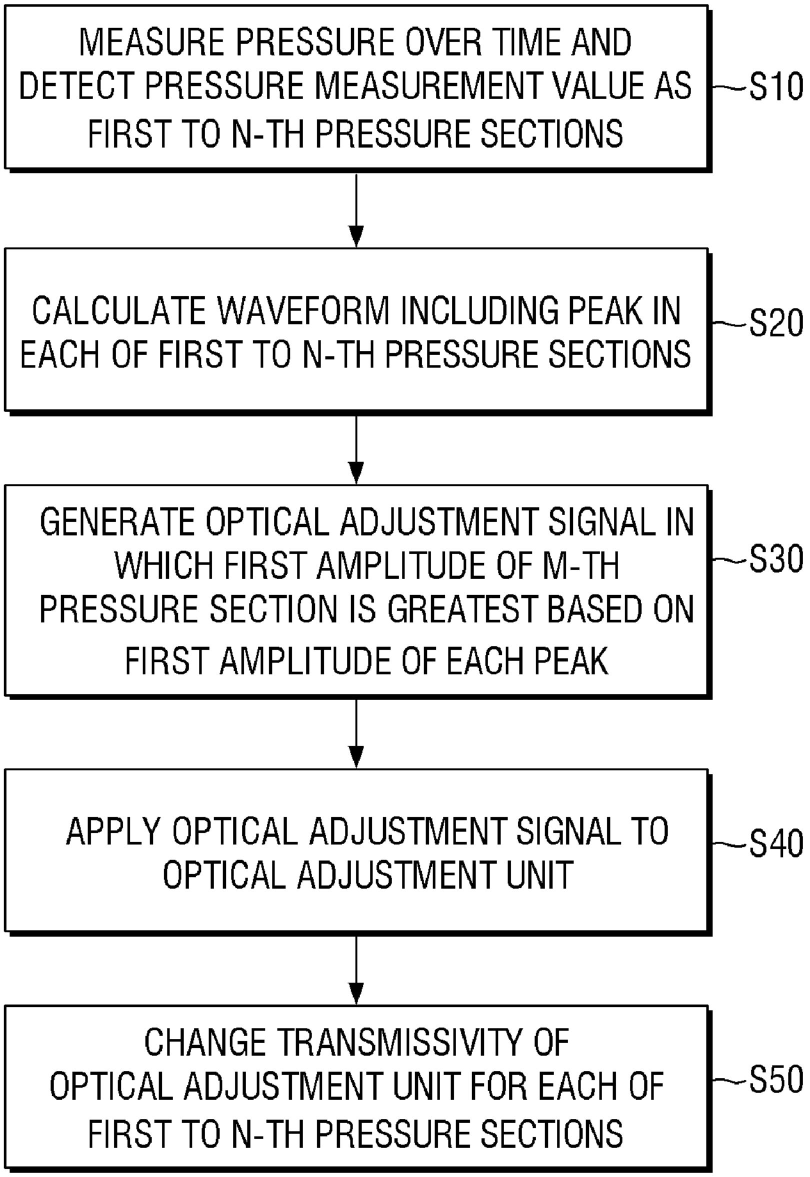
FIG. 7 is a flowchart illustrating a pulse wave light generation method of the pulse wave generation apparatus according to an embodiment.
Figure 8:
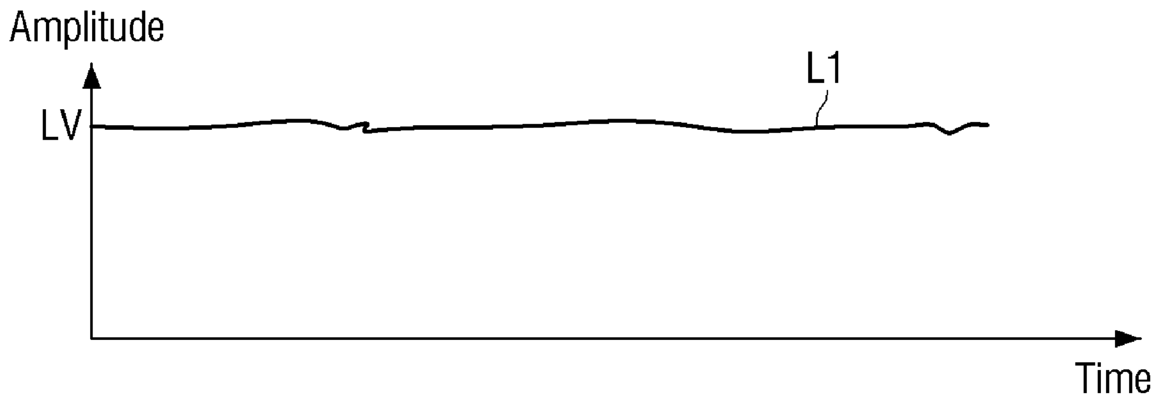
FIG. 8 is a graph illustrating incident light according to an embodiment.
Figure 9:
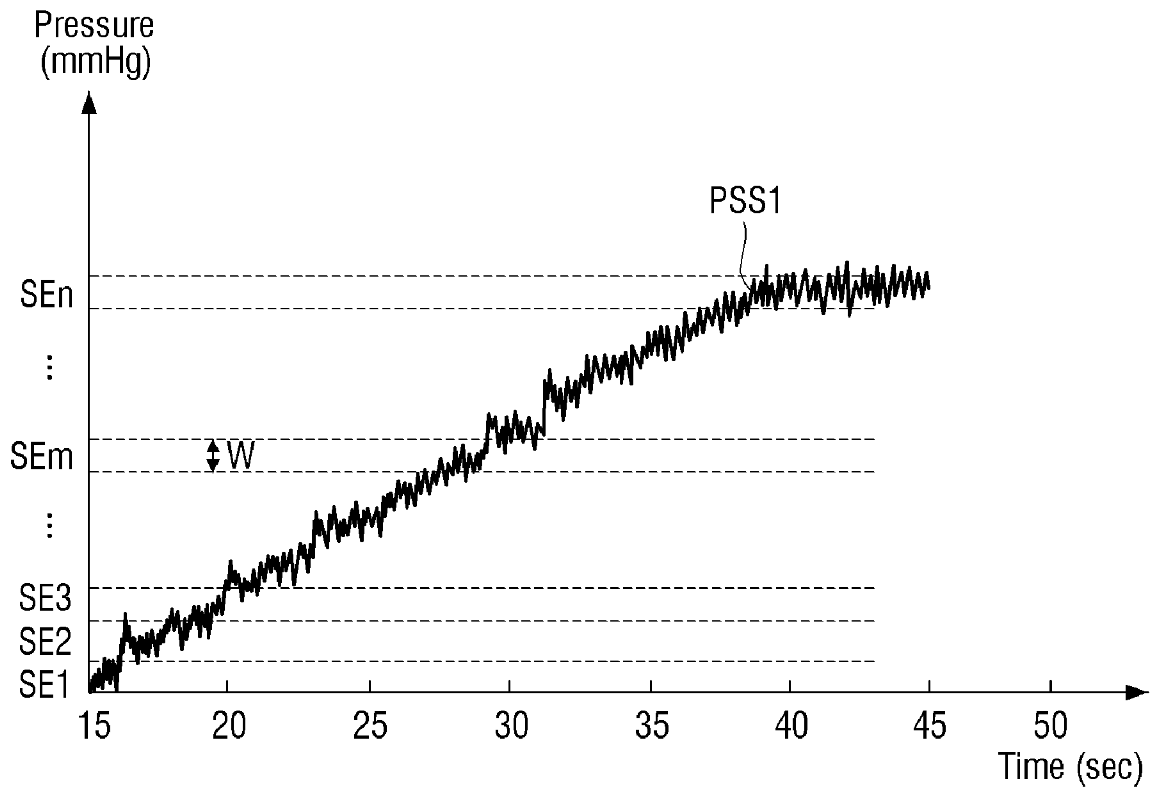
FIG. 9 is a graph illustrating a pressure measurement value according to a pressure applying time.
Figure 10:
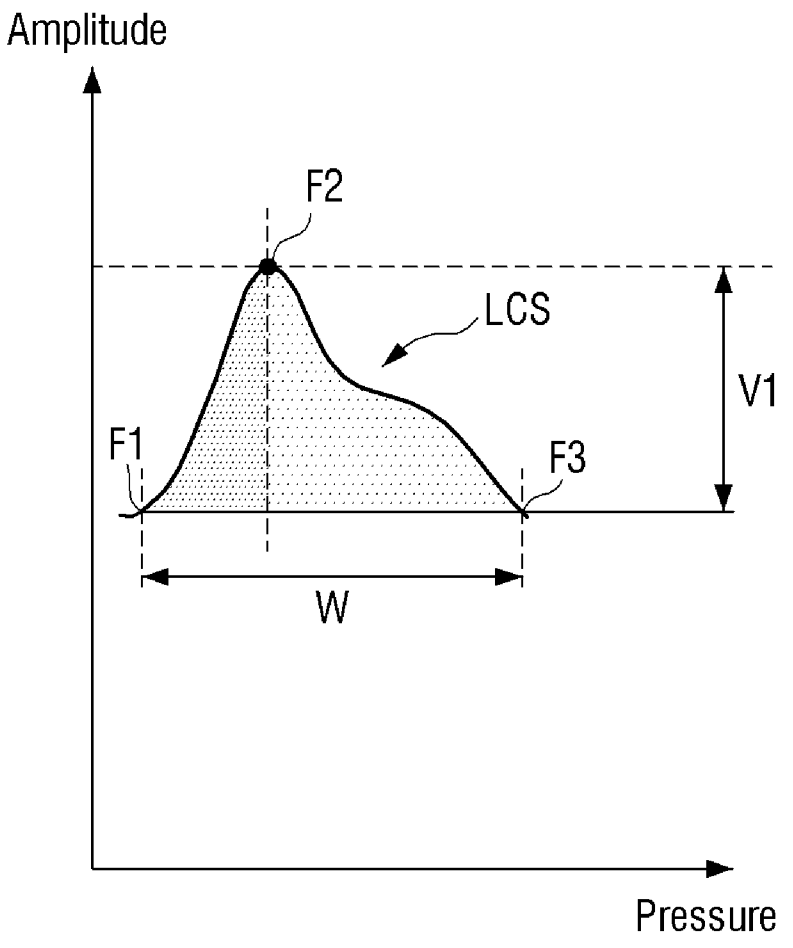
FIG. 10 is a graph illustrating a waveform of an optical adjustment signal according to an embodiment.
Figure 11:
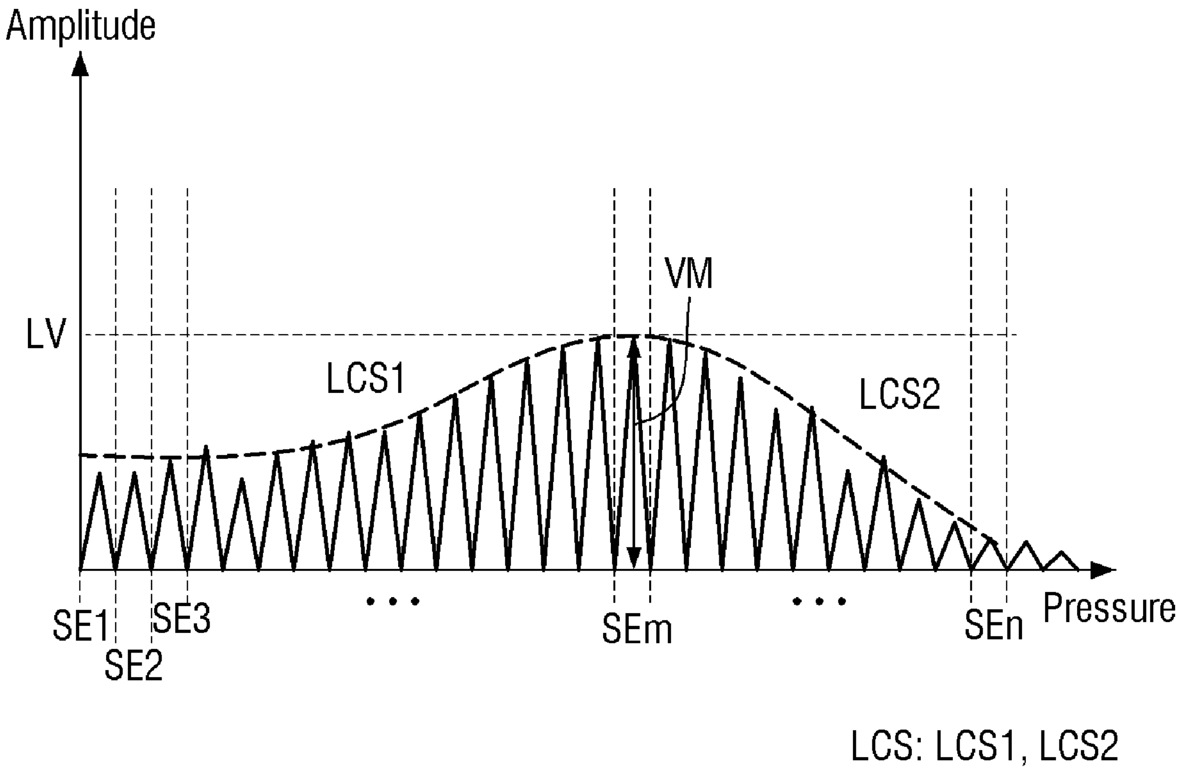
FIG. 11 is a graph illustrating the optical adjustment signal according to an embodiment.
Figure 12:
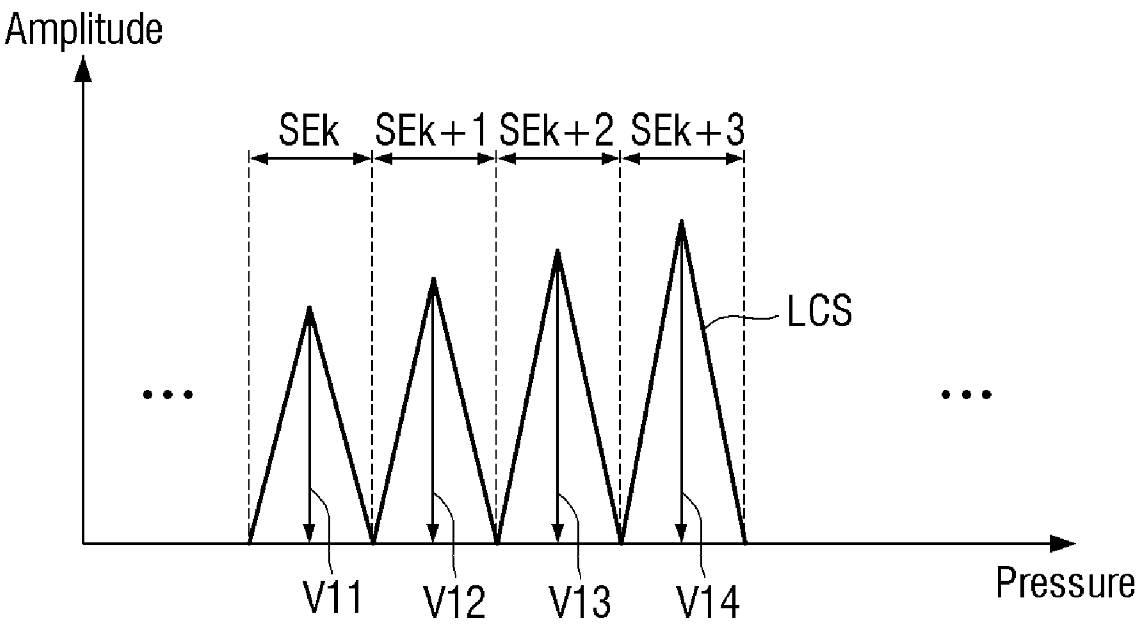
FIG. 12 is an enlarged graph of the optical adjustment signal of FIG. 11.
Figure 13:
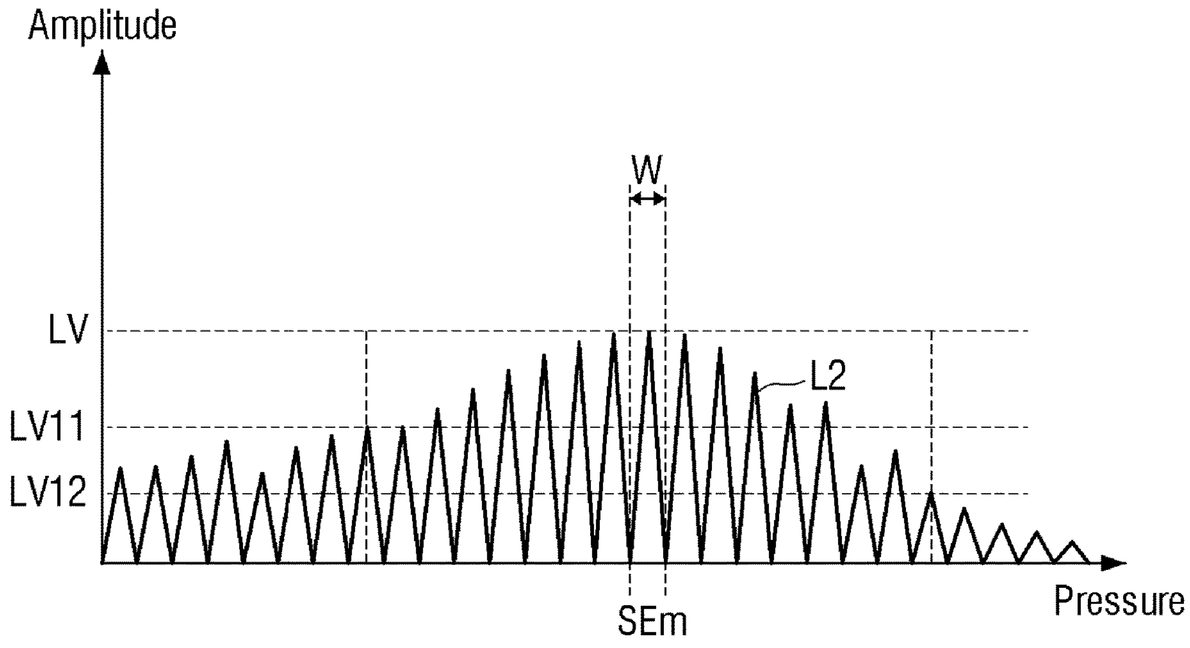
FIGS. 13 and 14 are graphs illustrating pulse wave light according to an embodiment.
Figure 14:
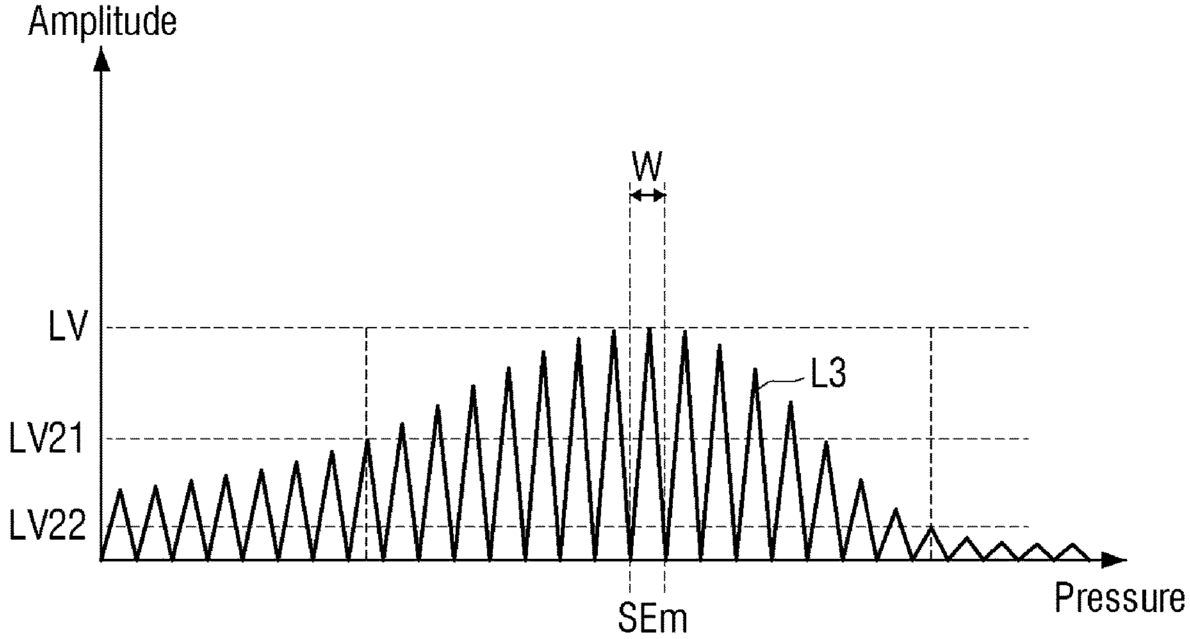

FIG. 7 is a flowchart illustrating a pulse wave light generation method of the pulse wave generation apparatus according to an embodiment. FIG. 8 is a graph illustrating incident light according to an embodiment. FIG. 9 is a graph illustrating a pressure measurement value according to a pressure applying time. FIG. 10 is a graph illustrating a waveform of an optical adjustment signal according to an embodiment. FIG. 11 is a graph illustrating the optical adjustment signal according to an embodiment. FIG. 12 is an enlarged graph of the optical adjustment signal of FIG. 11. FIGS. 13 and 14 are graphs illustrating pulse wave light according to an embodiment.

Referring to FIG. 7, first, the pressure sensor 24 may measure a pressure over time, and the control unit 25 may detect a pressure measurement value as first to N-th pressure sections SE1 to SEn (S10).

A method for generating the pulse wave light L2 and L3 in the blood pressure calculation system, according to an embodiment, will be described with reference to FIG. 8. The display device 1 may be disposed on one surface of the pulse wave generation apparatus 2, and the display device 1 may emit the incident light L1 toward one surface of the pulse wave generation apparatus 2. The incident light L1 emitted by the display device 1 may have a constant value over time. For example, the display device 1 may emit the incident light L1 having a first intensity LV to the pulse wave generation apparatus 2.

Referring further to FIG. 9, when the display device 1 emits the incident light L1 to the pulse wave generation apparatus 2, the user may apply a pressure to the pulse wave generation apparatus 2. The pressure sensor 24 may measure a pressure measurement value of the pressure applied by the user. A method for generating the pulse wave light L2 and L3 will be described in detail. For example, in a process in which the user brings his/her finger into contact with the pulse wave generation apparatus, the pressure measurement value measured by the pressure sensor 24 may gradually increase over time to reach a maximum value. Accordingly, the control unit 25 may receive the pressure measurement value over time measured by the pressure sensor 24.

In addition, the control unit 25 may detect the pressure measurement value as the first to N-th pressure sections SE1 to SEn. For example, the control unit 25 may divide the pressure measurement value over time into pressure sections having a constant pressure width W. Here, N is a positive integer. For example, the first to N-th pressure sections SE1 to SEn may have the constant pressure width W, respectively. However, the disclosure is not necessarily limited thereto, and a pressure width W of an M-th pressure section SEm, which is any one of the first to N-th pressure sections SE1 to SEn, may also be different from a pressure width W of the other pressure sections.

Next, the control unit 25 calculates a waveform including a peak in each of the first to N-th pressure sections SE1 to SEn (S20).

The pulse wave light L2 and L3 may have waveforms similar to that of the light reflected from the blood vessel of the human body. For example, during systole of the heart, blood ejected from the left ventricle of the heart moves to peripheral tissues, such that a blood volume in the arterial side increases. In addition, during the systole of the heart, red blood cells carry more oxyhemoglobin to the peripheral tissues. During diastole of the heart, there is partial suction of blood from the peripheral tissues toward the heart. In this case, when a peripheral blood vessel is exposed to light emitted from the pixel PX, the light may be absorbed by a peripheral tissue. Absorbance is dependent on a hematocrit and a blood volume. The absorbance may have a maximum value during the systole of the heart and a minimum value during the diastole of the heart. Accordingly, in a case where the display device 1 senses the pulse wave light L2 and L3 reflected from the pulse wave generation apparatus 2, the pulse wave light L2 and L3 may include a peak in each of the first to N-th pressure sections SE1 to SEn as in a case where the display device 1 senses the light reflected from the blood vessel of the human body.

Accordingly, the control unit 25 may calculate the waveform including the peak in each of the first to N-th pressure sections SE1 to SEn. Referring to FIG. 10, for example, the optical adjustment signal LCS may have each width W and feature points FF. One width W of the optical adjustment signal LCS may be defined as, for example, a time from the lowest point to the next lowest point. In addition, when a waveform of the optical adjustment signal LCS is viewed in units of width W, signal waveforms having a substantially similar shape may be repeated in the optical adjustment signal LCS.

The feature points FF may be defined by inflection points of a waveform formed within one width W. For example, the feature points FF may include a first feature point F1 positioned at the lowest point and a third feature point F3 positioned at the lowest point next to the lowest point, in one width W of the optical adjustment signal LCS. In this case, one width W may be defined as a length from the first feature point F1 to the third feature point F3. In addition, the feature points FF may include a second feature point F2 positioned at the highest point in one width W of the optical adjustment signal LCS. The second feature point F2 may be an upward convex peak in one width W of the optical adjustment signal LCS. At the second feature point F2, the optical adjustment signal LCS may have a first amplitude V1, which is a peak value in one width W. The first amplitude V1 may be a maximum magnitude of the optical adjustment signal LCS in one width W. In this case, the first amplitude V1 may be a difference between a value of the optical adjustment signal LCS at the first feature point F1 and a value of the optical adjustment signal LCS at the second feature point F2.

Thus, the control unit 25 may calculate the waveform having the peak based on the feature points FF and the first amplitude V1 in each of the first to N-th pressure sections SE1 to SEn.

Next, the control unit 25 may generate the optical adjustment signal LCS in which an amplitude of the M-th pressure section SEm is the greatest based on an amplitude of each peak (S30).

Referring to FIGS. 11 and 10, for example, the control unit 25 may calculate peak values (e.g., amplitudes) of first to M-th optical adjustment signals LCS so that the optical adjustment signal LCS sequentially increases in first to M-th pressure sections (where M is an integer greater than 1 and smaller than N). In addition, the control unit 25 may calculate peak values (e.g., amplitudes) of M-th to N-th optical adjustment signals LCS so that the optical adjustment signal LCS sequentially decreases in M-th to N-th pressure sections SEm to SEn. For example, the control unit 25 may calculate a first optical adjustment signal LCS1 that sequentially increases in the first to M-th pressure sections SE1 to SEm and calculate a second optical adjustment signal LCS2 that sequentially decreases in the M-th to N-th pressure sections SEm to SEn. Accordingly, in the optical adjustment signal LCS, the first amplitude VM of the M-th pressure section SEm may have a maximum value. In addition, the first amplitude VM of the M-th pressure section SEm may have the same value as the first intensity LV of the incident light L1.

Referring further to FIG. 12, the first optical adjustment signal LCS1 may sequentially increase as a pressure increases. For example, a 1_k+1-th amplitude V12 of a k+1-th pressure section SEk+1 may be greater than a 1_k-th amplitude V11 of a k-th pressure section SEk, a 1_k+2-th amplitude V13 of a k+2-th pressure section SEk+2 may be greater than the 1_k+1-th amplitude V12 of the k+1-th pressure section SEk+1, and a 1_k+3-th amplitude V14 of a k+3-th pressure section SEk+3 may be greater than the 1_k+2-th amplitude V13 of the k+2-th pressure section SEk+2. In addition, the second optical adjustment signal LCS2 may sequentially decrease as a pressure increases.

The control unit 25 may control the optical adjustment signal LCS so that the pulse wave light L2 and L3 reflected from the pulse wave generation apparatus 2 are similar to the light reflected from the blood vessel of the human body. However, the incident light L1 emitted from the display device 1 may be transmitted through the optical adjustment unit 22 twice while being reflected by the reflection unit 23.

For example, the incident light L1 emitted from the display device 1 may be transmitted through the optical adjustment unit 22, such that the first pulse wave light L2 may be generated, and the first pulse wave light L2 may be reflected by the reflection unit 23 and be retransmitted through the optical adjustment unit 22, such that the second pulse wave light L3 may be generated. In this case, since the second pulse wave light L3 should be similar to the light reflected by the blood vessel of the human body, the first pulse wave light L2 may be different from the light reflected by the blood vessel of the human body. This will be described later with reference to FIGS. 13 and 14.

Finally, the control unit 25 may apply the optical adjustment signal LCS to the optical adjustment unit 22 (S40), and the transmissivity of the optical adjustment unit 22 may be changed for each of the first to N-th pressure sections SE1 to SEn (S50).

The optical adjustment unit 22 may receive the optical adjustment signal LCS from the control unit 25. The transmissivity of the optical adjustment unit 22 may be changed according to the amplitude of the optical adjustment signal LCS. For example, when the optical adjustment signal LCS sequentially increases in the first to M-th pressure sections SE1 to SEm and sequentially decreases in the M-th to N-th pressure sections SEm to SEn, the transmissivity of the optical adjustment unit 22 may sequentially increase in the first to M-th pressure sections SE1 to SEm and decrease sequentially in the M-th to N-th pressure sections SEm to SEn. In addition, when the optical adjustment signal LCS has a maximum amplitude in the M-th pressure section SEm, the transmissivity of the optical adjustment unit 22 may be the greatest.

The optical adjustment signal LCS may be applied to the supply electrodes 228 of the optical adjustment unit 22. Accordingly, the lower electrode 222 and the upper electrode 225 may have a voltage difference corresponding to the amplitude of the optical adjustment signal LCS. Accordingly, the transmissivity of the electrochromic layer 223 may be determined according to a voltage difference between the upper electrode 225 and the lower electrode 222.

FIG. 13 is a graph illustrating the first pulse wave light L2 generated by allowing the incident light L1 emitted from the pixel PX of the display device 1 to be transmitted through the optical adjustment unit 22. FIG. 14 is a graph illustrating the second pulse wave light L3 generated by allowing the first pulse wave light L2 to be reflected by the reflection unit 23 and be retransmitted through the optical adjustment unit 22. The light reflected from the blood vessel of the human body may be similar to the second pulse wave light L3 of FIG. 14. However, the incident light L1 emitted from the display device 1 may be retransmitted through the optical adjustment unit 22 while being reflected by the reflection unit 23.

Accordingly, the control unit 25 may control the transmissivity of the optical adjustment unit 22 so that the light retransmitted through the optical adjustment unit 22 is similar to the light reflected from the blood vessel of the human body. For example, the control unit 25 may perform control so that an eleventh light intensity LV11 of any one section of the first pulse wave light L2 is greater than a twenty first light intensity LV21 of any one section of the second pulse wave light L3. In addition, the control unit 25 may perform control so that a twelfth light intensity LV12 of another section of the first pulse wave light L2 is greater than a twenty second light intensity LV22 of another section of the second pulse wave light L3.

The control unit 25 may use a linear regression analysis in order to adjust the light retransmitted through the optical adjustment unit 22 to be similar to the light reflected from the blood vessel of the human body. For example, the control unit 25 may use a curve fitting method or change the optical adjustment signal LCS based on a lookup table (LUT). Accordingly, the second pulse wave light L3 retransmitted through the optical adjustment unit 22 may become similar to the light reflected from the blood vessel of the human body.

The pulse wave generation apparatus 2, according to the embodiment, may generate the optical adjustment signal LCS according to the pressure to test a pulse wave or blood pressure measurement of the display device 1. The pulse wave generation apparatus 2 may perform control so that the pulse wave light L2 and L3 reflected from the pulse wave generation apparatus 2 are similar to the light reflected from the blood vessel of the human body by adjusting the transmissivity of the optical adjustment unit 22. Accordingly, the photo-sensor PS of the display device 1 may sense the pulse wave light L2 and L3 to calculate the blood pressure. For example, the pulse wave generation apparatus 2 may simulate the pulse wave signal PPG of the human body, and the display device 1 may calculate the blood pressure based on the pulse wave light L2 and L3 reflected from the pulse wave generation apparatus 2.

In addition, since the pulse wave light L2 and L3 reflected from the pulse wave generation apparatus 2 may be freely adjusted by adjusting the optical adjustment signal LCS of the pulse wave generation apparatus 2, a pulse wave change according to various health conditions of the human body may also be tested.

Figure 15:
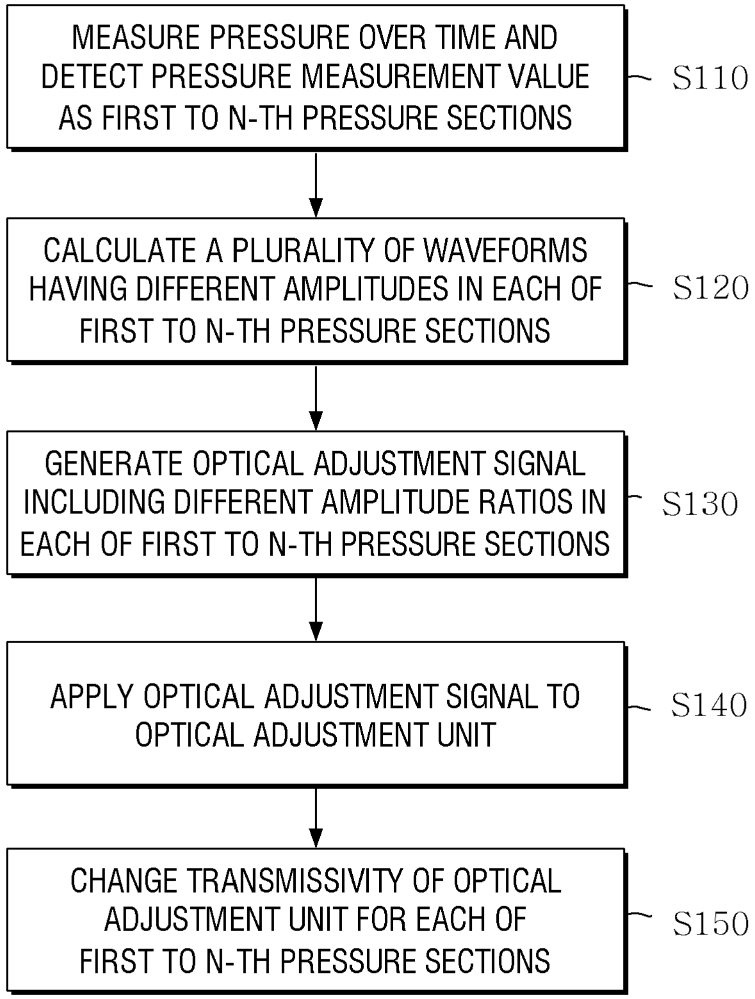
FIG. 15 is a flowchart illustrating a pulse wave light generation method of the pulse wave generation apparatus according to an embodiment.
Figure 16:
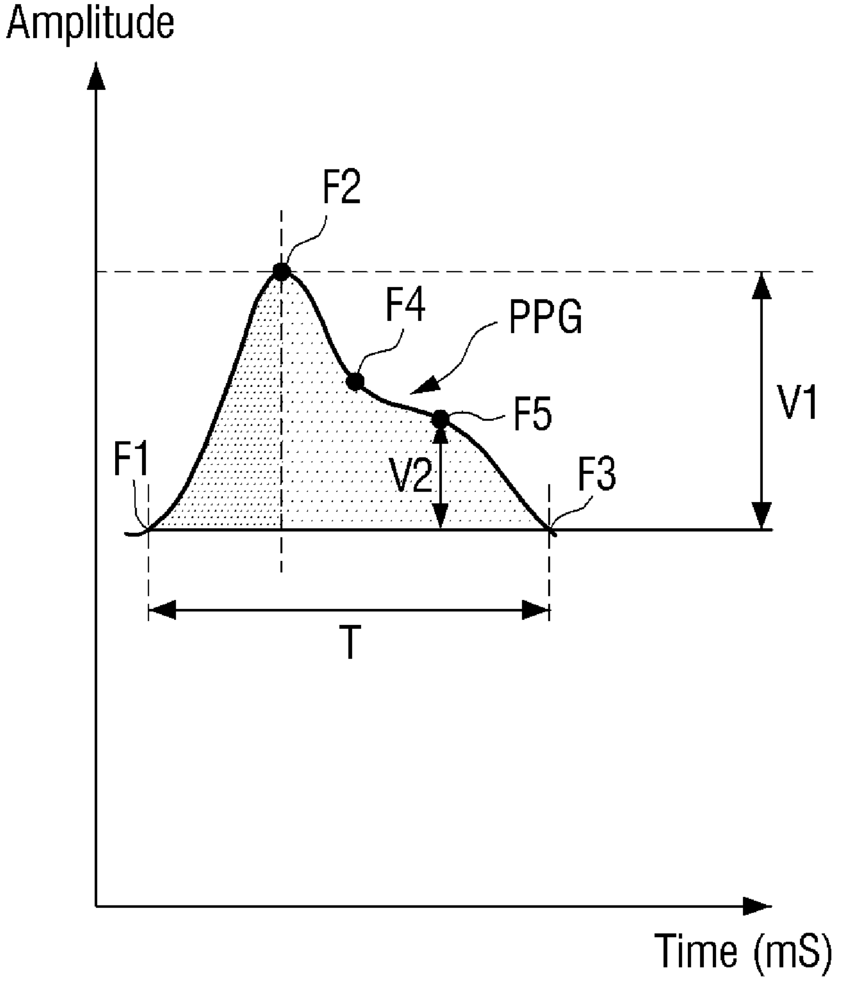
FIG. 16 is a graph illustrating a waveform of an optical adjustment signal according to an embodiment.
Figure 17:
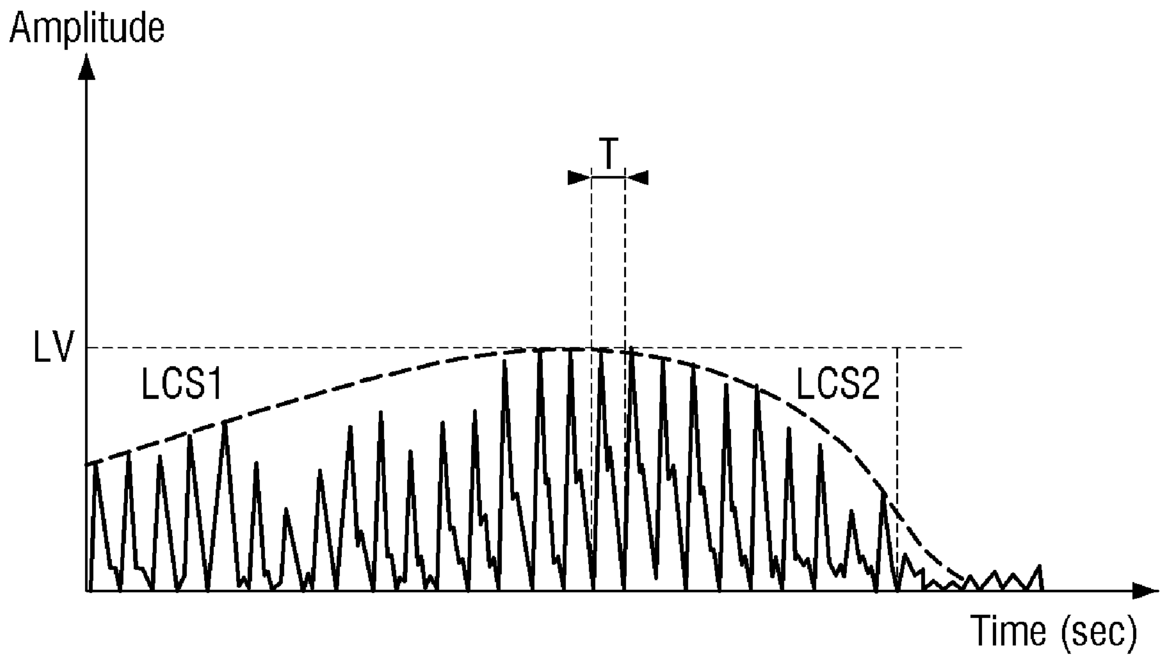
FIG. 17 is a graph illustrating the optical adjustment signal according to an embodiment.
Figure 18:
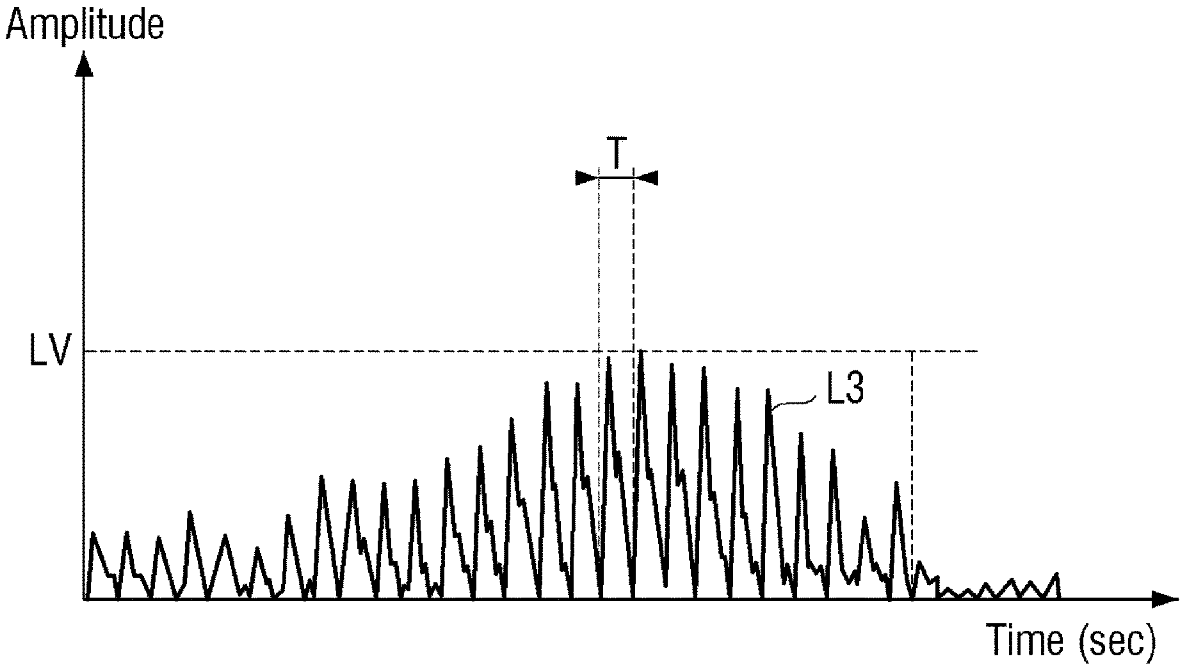
FIG. 18 is a graph illustrating a pulse wave light according to an embodiment.
Figure 19:
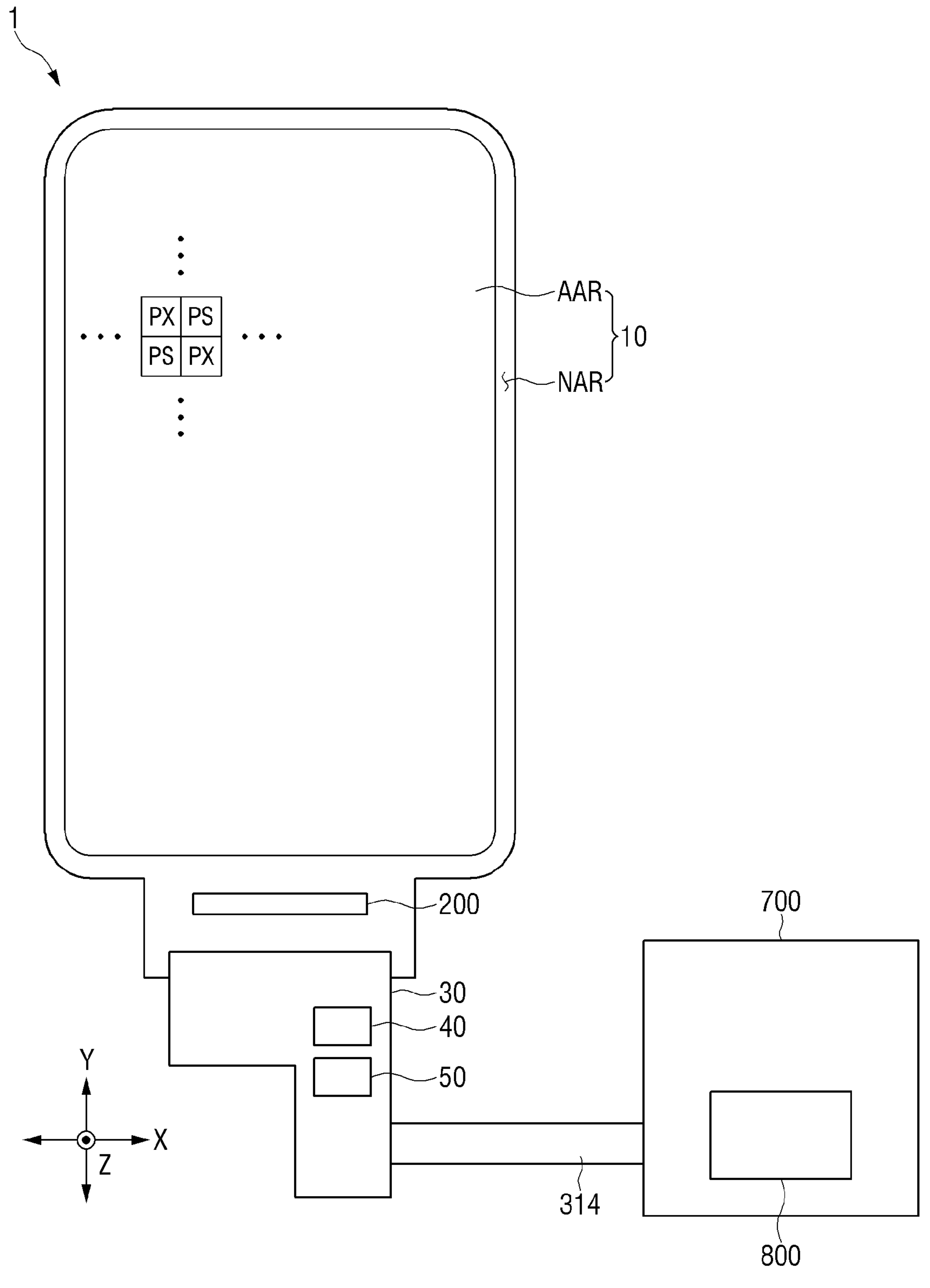
FIG. 19 is a plan view of the display device according to an embodiment.

FIG. 15 is a flowchart illustrating a pulse wave light generation method of the pulse wave generation apparatus according to an embodiment. FIG. 16 is a graph illustrating a waveform of an optical adjustment signal according to an embodiment. FIG. 17 is a graph illustrating the optical adjustment signal according to an embodiment. FIGS. 18 and 19 are graphs illustrating pulse wave light according to an embodiment.

Referring to FIG. 15, first, the pressure sensor 24 may measure a pressure over time, and the control unit 25 may detect a pressure measurement value as first to N-th pressure sections SE1 to SEn (S110). A description thereof is substantially the same as the arrangement of FIG. 7, and thus, to the extent that a description of an element is omitted, it is to be assumed that the element is at least similar to a corresponding element described above with respect to FIG. 7.

Next, the control unit 25 calculates a plurality of waveforms having different amplitudes (S120). As described above, the pulse wave light L2 and L3 may have waveforms similar to that of the light reflected from the blood vessel of the human body. For example, a pulse wave of a person has a plurality of waveforms having different amplitudes even between the systole and the diastole of the heart.

Accordingly, the control unit 25 may calculate a plurality of waveforms having different amplitudes in each of the first to N-th pressure sections SE1 to SEn. For example, referring to FIG. 16, for example, the optical adjustment signal LCS may have each cycle and feature points FF. One cycle of the optical adjustment signal LCS may be defined as, for example, a time from the lowest point to the next lowest point. In addition, when a waveform of the optical adjustment signal LCS is viewed in units of cycle, signal waveforms having a substantially similar shape may be repeated in the optical adjustment signal LCS. The optical adjustment signal LCS may further include points having blood pressure information and biometric information for each user as well as the first to third feature points as shown in FIG. 10. For example, the optical adjustment signal LCS may further include a fourth feature point F4 positioned between the second feature point F2 and the third feature point F3 and downward convex and a fifth feature point F5 positioned between the second feature point F2 and the third feature point F3 and upward convex. In addition, the optical adjustment signal LCS may further include a second amplitude V2, which is a peak value in one cycle of the optical adjustment signal LCS at the fifth feature point F5.

Thus, the control unit 25 may calculate the plurality of waveforms having the different amplitudes based on the feature points FF, the first amplitude V1, and the second amplitude V2 in each of the first to N-th pressure sections SE1 to SEn.

Next, the control unit 25 generates the optical adjustment signal LCS including different amplitude ratios in each of the first to N-th pressure sections SE1 to SEn (S130).

Referring to FIG. 17, the control unit 25 may calculate peak values (e.g., amplitudes) of first to M-th optical adjustment signals LCS so that the optical adjustment signal LCS sequentially increases in first to M-th pressure sections (where M is an integer greater than 1 and smaller than N) as shown in FIG. 11. A description thereof is substantially the same as the arrangement of FIG. 11, and thus, to the extent that a description of an element is omitted, it may be assumed that the element is at least similar to that of a corresponding element shown in FIG. 11.

In addition, as described above, the optical adjustment signal LCS may include a waveform having the first amplitude V1 and the second amplitude V2 for each cycle of the optical adjustment signal LCS. In this case, a ratio between the first amplitude V1 and the second amplitude V2 may be different for each cycle of the optical adjustment signal LCS.

The control unit 25 may apply the optical adjustment signal LCS to the optical adjustment unit 22 (S140), and may change the transmissivity in the first to N-th pressure sections SE1 to SEn (S150). Accordingly, the transmissivity of the optical adjustment unit 22 may be changed according to the optical adjustment signal LCS. For example, when a pressure is gradually applied to the pulse wave generation apparatus 2, the optical adjustment unit 22 may be adjusted to have different transmissivities in each of the first to N-th pressure sections SE1 to SEn. Accordingly, as in a case of FIG. 18, the second pulse wave light L3 may have a plurality of waveforms having different intensities in each of the first to N-th pressure sections SE1 to SEn.

Also in a case of the embodiment, the pulse wave generation apparatus 2 may generate the optical adjustment signal LCS according to the pressure to test a pulse wave or blood pressure measurement of the display device 1. The pulse wave generation apparatus 2 may perform control so that the pulse wave light L2 and L3 reflected from the pulse wave generation apparatus 2 are similar to the light reflected from the blood vessel of the human body by adjusting the transmissivity of the optical adjustment unit 22. Accordingly, the photo-sensor PS of the display device 1 may sense the pulse wave light L2 and L3 to calculate the blood pressure. For example, the pulse wave generation apparatus 2 may simulate the pulse wave signal PPG of the human body, and the display device 1 may calculate the blood pressure based on the pulse wave light L2 and L3 reflected from the pulse wave generation apparatus 2. In addition, since the pulse wave light L2 and L3 reflected from the pulse wave generation apparatus 2 may be freely adjusted by adjusting the optical adjustment signal LCS of the pulse wave generation apparatus 2, a pulse wave change according to various health conditions of the human body may also be tested.

Figure 20:
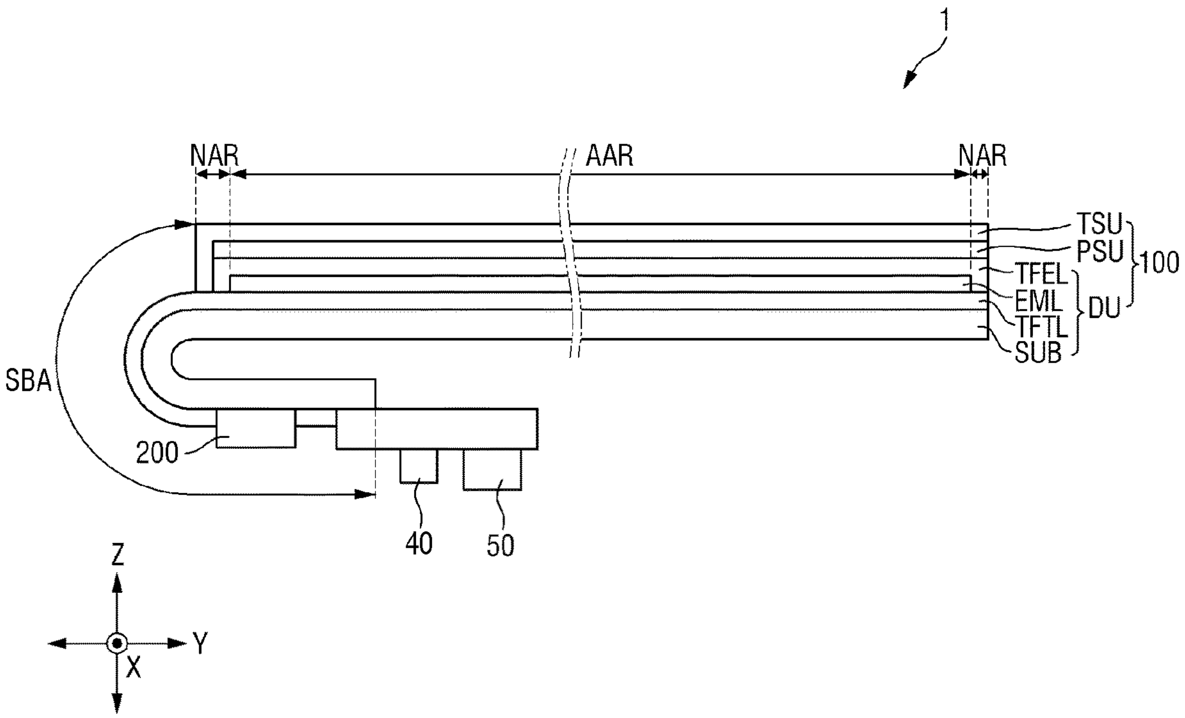
FIG. 20 is a cross-sectional view of the display device according to an embodiment.

FIG. 19 is a plan view of the display device according to an embodiment. FIG. 20 is a cross-sectional view of the display device according to an embodiment.

Referring to FIG. 19, the display device 1 may include various electronic devices providing a display screen. Examples of the display device 1 may include, but are not necessarily limited to including, mobile phones, smartphones, tablet personal computers (PCs), mobile communication terminals, electronic notebooks, electronic books, personal digital assistants (PDAs), portable multimedia players (PMPs), navigation devices, ultra mobile PCs (UMPCs), televisions, game machines, wrist watch-type electronic devices, head-mounted displays, monitors of personal computers, laptop computers, vehicle instrument boards, digital cameras, camcorders, external digital billboards, electric signs, various medical devices, various inspection devices, various home appliances including display areas, such as refrigerators and washing machines, Internet of Things (IoT) devices, or the like. Representative examples of a display device 1 to be described later may include smartphones, tablet PCs, laptop computers, or the like, but are not necessarily limited thereto.

The display device 1 may include a display panel 10, a display driver 200, a circuit board 30, a pulse wave sensing circuit 50, a pressure sensing circuit 40, a main circuit board 700, and a main processor 800.

The display panel 10 may include an active area AAR and a non-active area NAR.

The active area AAR includes a display area in which a screen is displayed. The active area AAR may completely overlap the display area. A plurality of pixels PX displaying an image may be disposed in the display area. Each pixel PX may include a light emitting unit emitting light.

The active area AAR further includes a light sensing area. The light sensing area is an area responding to light, and is an area configured to sense an amount, a wavelength, or the like, of incident light. The light sensing area may overlap the display area. In an embodiment, the light sensing area may completely overlap the active area AAR, for example, in a plan view. In this case, the light sensing area and the display area may be the same as each other. In an embodiment, the light sensing area may be disposed only in a portion of the active area AAR. For example, the light sensing area may be disposed only in a limited area required for fingerprint recognition. In this case, the light sensing area may overlap a portion of the display area, but might not overlap another portion of the display area.

A plurality of photo-sensors PS responding to light may be disposed in the light sensing area.

The non-active area NAR may be disposed around the active area AAR. The display driver 200 may be disposed in the non-active area NAR. The display driver 200 may drive the plurality of pixels PX and/or the plurality of photo-sensors PS. The display driver 200 may output signals and voltages for driving the display panel 10. The display driver 200 may be formed as an integrated circuit (IC) and be mounted on the display panel 10. Signal lines for transferring signals between the display driver 200 and the active area AAR may be further disposed in the non-active area NAR. As an example, the display driver 200 may be mounted on the circuit board 30.

The circuit board 30 may be attached to one end of the display panel 10 using an anisotropic conductive film (ACF). Lead lines of the circuit board 30 may be electrically connected to pad parts of the display panel 10. The circuit board 30 may be a flexible printed circuit board or a flexible film such as a chip on film.

The pulse wave sensing circuit 50 may be disposed on the circuit board 30. The pulse wave sensing circuit 50 may be formed as an integrated circuit and be attached to an upper surface of the circuit board 30. The pulse wave sensing circuit 50 may be connected to a display layer of the display panel 10. A pulse wave sensing circuit 50 may sense a photocurrent generated by photocharges incident on the plurality of photo-sensors PS of the display panel 10. The pulse wave sensing circuit 50 may recognize a pulse wave of a user based on the photocurrent.

The pressure sensing circuit 40 may be disposed on the circuit board 30. The pressure sensing circuit 40 may be formed as an integrated circuit and be attached to the upper surface of the circuit board 30. The pressure sensing circuit 40 may be connected to the display layer of the display panel 10. The pressure sensing circuit 40 may sense an electrical signal by a pressure applied to the pressure sensing unit of the display panel 10. The pressure sensing circuit 40 may generate pressure data according to a change in the electrical signal sensed by the pressure sensing unit, and transmit the pressure data to the main processor 800.

The main circuit board 700 may be a printed circuit board or a flexible printed circuit board.

The main circuit board 700 may include the main processor 800.

The main processor 800 may control all functions of the display device 1. For example, the main processor 800 may output digital video data to the display driver 200 through the circuit board 30 so that the display panel 10 displays an image. In addition, the main processor 800 may receive touch data from a touch driving circuit, decide touch coordinates of the user, and then execute an application indicated by an icon displayed on the touch coordinates of the user.

The main processor 800 may calculate a pulse wave signal PPG reflecting a blood change depending on a heartbeat according to an optical signal input from the pulse wave sensing circuit 50. In addition, the main processor 800 may calculate a touch pressure of the user according to the electrical signal input from the pressure sensing circuit 40. In addition, the main processor 800 may calculate a blood pressure of the user based on the pulse wave signal PPG and a pressure signal.

The main processor 800 may be an application processor formed of an integrated circuit, a central processing unit, or a system chip. In addition, a mobile communication module capable of transmitting and receiving wireless signals to and from at least one of a base station, an external terminal, and a server over a mobile communication network may be further mounted on the main circuit board 700. The wireless signal may include various types of data according to transmission/reception of a voice signal, a video call signal, or a text/multimedia message.

Referring further to FIG. 20, the display device 1 includes the display panel, the display driver 200, a touch sensing unit TSU, a pressure sensing unit PSU, the pulse wave sensing circuit and a touch driver A sub-area SBA may protrude from one side of the non-active area NAR in a second direction Y. A length of the sub-area SBA in the second direction Y may be smaller than a length of the non-active area NAR in the second direction Y. A length of the sub-area SBA in a first direction X may be smaller than or substantially the same as a length of the non-active area NAR in the first direction X.

The display driver 200 may be disposed in the sub-area SBA. The display driver 200 may be attached to driving pads using a conductive adhesive member such as an anisotropic conductive film. The sub-area SBA may be bent. In this case, the sub-area SBA may be disposed below the active area AAR. The sub-area SBA may overlap the active area AAR in a third direction Z.

The pressure sensing unit PSU sensing a pressure applied by a body part such as a finger may be disposed on a front surface portion of the display panel 10. The pressure sensing unit PSU may be formed in a transparent sheet type in which a plurality of transparent electrodes are arranged in vertical and horizontal directions, and may be disposed on a front surface of the non-active area NAR.

The touch sensing unit TSU sensing the body part such as the finger may be disposed on a front surface portion of the pressure sensing unit PSU as well as in the active area AAR. The touch sensing unit TSU may include a plurality of touch electrodes to sense a user's touch in a capacitive manner. The touch sensing unit TSU includes the plurality of touch electrodes arranged to cross each other in the first and second directions X and Y. For example, the plurality of touch electrodes include a plurality of driving electrodes spaced apart from each other in parallel in the first direction X and a plurality of sensing electrodes spaced apart from each other in parallel in the second direction Y so as to cross the plurality of driving electrodes with an organic material layer or an inorganic material layer interposed therebetween. The plurality of driving electrodes and sensing electrodes may extend in a line area between the pixels and the photo-sensors (or an image non-display area in which lines are formed) so as not to overlap the respective pixels PX and photo-sensors PS arranged in the active area AAR.

The pressure sensing unit PSU includes a plurality of pressure sensing electrodes arranged to cross each other in the first and second directions X and Y. For example, the plurality of pressure sensing electrodes include a plurality of lower electrodes spaced apart from each other in parallel in the first direction X and a plurality of upper electrodes spaced apart from each other in parallel in the second direction Y so as to cross the plurality of lower electrodes with a transparent inorganic (or organic) material layer interposed therebetween. The plurality of lower electrodes and upper electrodes may extend in the line area between the pixels and the photo-sensors (or the image non-display area in which the lines are formed) so as not to overlap the respective pixels and photo-sensors arranged in the active area AAR. The plurality of lower electrodes and upper electrodes form self-capacitance with the transparent inorganic (or organic) material layer interposed therebetween, and transmit pressure sensing signals that vary according to a touch pressure of the user to the touch driver 500.

The circuit board may be attached to one end of the sub-area SBA. Therefore, the circuit board may be electrically connected to the display panel 10 and the display driver 200. The display panel 10 and the display driver 200 may receive digital video data, timing signals, and driving voltages through the circuit board. The circuit board may be a flexible printed circuit board, a printed circuit board, or a flexible film such as a chip on film.

The display driver 200 may generate digital data and electrical control signals for driving the display panel 10. Each of the pulse wave sensing circuit 50 and the pressure sensing circuit 40 as well as the display driver 200 may be formed as an integrated circuit (IC). Each of the display driver 200, the pulse wave sensing circuit 50, and the pressure sensing circuit 40 may be attached onto the display panel 10 or the circuit board in a chip on glass (COG) manner, a chip on plastic (COP) manner, or an ultrasonic bonding manner, but is not necessarily limited thereto. For example, the pulse wave sensing circuit 50 and the pressure sensing circuit 40 as well as the display driver 200 may be attached onto the circuit board in a chip on film (COF) manner.

Figure 21:
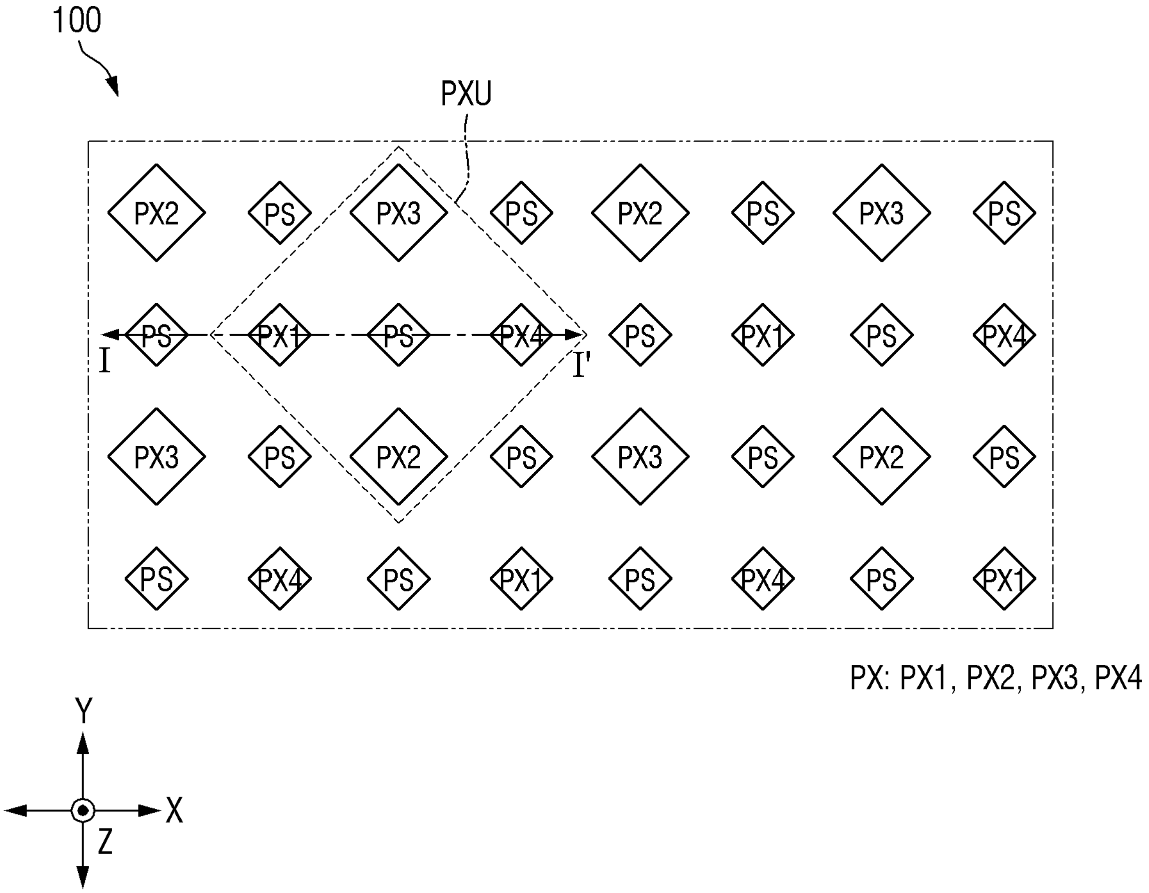
FIG. 21 is a plan layout view of pixels and photo-sensors of a display cell according to an embodiment.

FIG. 21 is a plan layout view of pixels and photo-sensors of a display cell according to an embodiment.

Referring to FIG. 21, a plurality of pixels PX and a plurality of photo-sensors PS may be repeatedly disposed in the display panel 10.

The plurality of pixels PX: PX1, PX2, PX3, and PX4 may include first sub-pixels PX1, second sub-pixels PX2, third sub-pixels PX3, and fourth sub-pixels PX4. For example, the second sub-pixels PX2 may emit light of a red wavelength, the first sub-pixels PX1 and the fourth sub-pixels PX4 may emit light of a green wavelength, and the third sub-pixels PX3 may emit light of a blue wavelength.

However, the disclosure is not necessarily limited thereto, and the first sub-pixels PX1 may emit green light and the second sub-pixels PX2 may emit infrared light. Alternatively, the first sub-pixels PX1 may emit blue or green light, and the second sub-pixels PX2 may emit red light or infrared light.

The plurality of pixels PX may include a plurality of emission areas emitting light, respectively. The plurality of photo-sensors PS may include a plurality of light sensing areas sensing light incident thereon.

The first sub-pixels PX1, the second sub-pixels PX2, the third sub-pixels PX3, and the fourth sub-pixels PX4 and the plurality of photo-sensors PS may be alternately arranged in the first direction X and the second direction Y. In an embodiment, the second sub-pixels PX2 and the third sub-pixels PX3 may be alternately arranged while forming a first row along the first direction X, and the first sub-pixels PX1 and the fourth sub-pixels PX4 may be repeatedly arranged along the first direction in a second row adjacent to the first row. Pixels PX belonging to the first row may be disposed to be misaligned with pixels PX belonging to the second row in the first direction X. Arrangements of the first row and the second row may be repeated up to an N-th row.

The photo-sensors PS may be disposed between the second sub-pixels PX2 and the third sub-pixels PX3 forming the first row and be disposed to be spaced apart from each other. The second sub-pixels PX2, the photo-sensors PS, and the third sub-pixels PX3 may be alternately arranged along the first direction X. The photo-sensors PS may be disposed between the first sub-pixels PX1 and the fourth sub-pixels PX4 forming the second row and be disposed to be spaced apart from each other. The first sub-pixels PX1, the photo-sensors PS, and the fourth sub-pixels PX4 may be alternately arranged along the first direction X. The number of photo-sensors PS in the first row may be the same as the number of photo-sensors PS in the second row. Arrangements of the first row and the second row may be repeated up to an N-th row.

As an example, the photo-sensors PS may be disposed between the first sub-pixels PX1 and the fourth sub-pixels PX4 forming the second row, and might not be disposed between the second sub-pixels PX2 and the third sub-pixels PX3 forming the first row. For example, the photo-sensors PS might not be disposed in the first row.

Sizes of emission areas of the respective pixels PX may be different from each other. Sizes of emission areas of the first sub-pixels PX1 and the fourth sub-pixels PX4 may be smaller than those of emission areas of the second sub-pixels PX2 or the third sub-pixels PX3. It has been illustrated in FIG. 21 that the respective pixels PX have a rhombic shape, but the disclosure is not necessarily limited thereto, and the respective pixels PX have may have a rectangular shape, an octagonal shape, a circular shape, or other polygonal shapes.

One pixel unit PXU may include one first sub-pixel PX1, one second sub-pixel PX2, one third sub-pixel PX3, and one fourth sub-pixel PX4. The pixel unit PXU refers to a group of color pixels capable of expressing a gradation.

Figure 22:
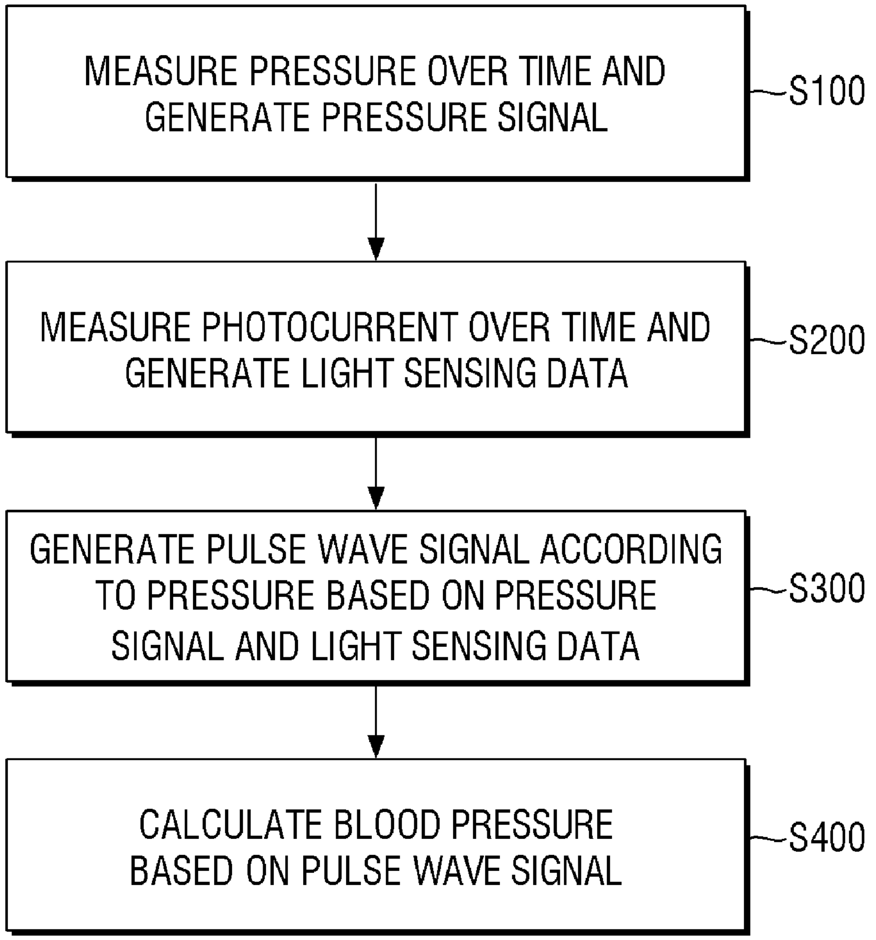
FIG. 22 is a flowchart illustrating a method of calculating a blood pressure by the display device according to an embodiment.
Figure 23:
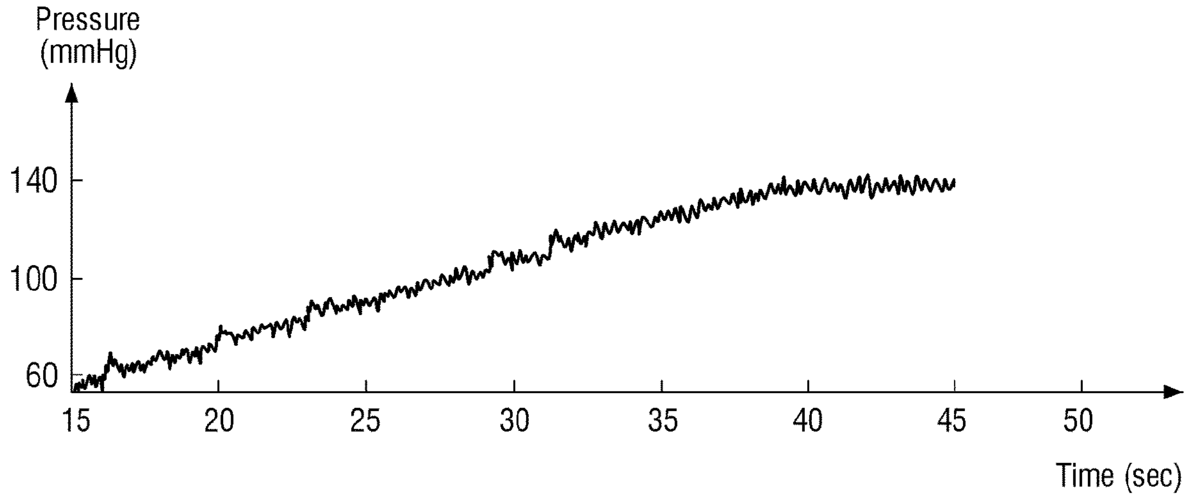
FIG. 23 is a graph illustrating a pressure measurement value according to a pressure applying time.

FIG. 22 is a flowchart illustrating a method of calculating a blood pressure by the display device according to an embodiment. FIG. 23 is a graph illustrating a pressure measurement value according to a pressure applying time. FIG. 24 is a graph illustrating a pulse wave signal over time.

A method of calculating a blood pressure based on the pulse wave signal PPG by the main processor 800 will be described with reference to FIGS. 22 to 24.

Referring to FIG. 22, first, the pressure sensing unit PSU measures a pressure over time, and the main processor 800 generates a pressure signal PSS based on a pressure measurement value (S100).

Referring further to FIG. 23, the user may apply a pressure to the pressure sensing unit PSU, and the pressure sensing unit PSU may measure a pressure measurement value of the pressure applied by the user. A method of generating the pulse wave signal PPG will be described in detail. For example, in a process in which the user brings his/her finger into contact with the display device 1, the pressure measurement value measured by the pressure sensing unit PSU may gradually increase over time to reach a maximum value. When the pressure measurement value (i.e., a contact pressure) increases, a blood vessel may be constricted, such that a blood flow rate may be decreased or become 0. Accordingly, the main processor 800 may receive the pressure signal PSS having the pressure measurement value over time, generated by the pressure sensing circuit 40.

Next, the photo-sensor PS may measure a photocurrent over time, and the main processor 800 may generate light sensing data based on a photocurrent value over time (S200).

Referring further to FIG. 24, in order to generate the pulse wave signal PPG, pulse wave information over time is also required together with the pressure data. During systole of the heart, blood ejected from the left ventricle of the heart moves to peripheral tissues, such that a blood volume in the arterial side increases. In addition, during the systole of the heart, red blood cells carry more oxyhemoglobin to the peripheral tissues. During diastole of the heart, there is partial suction of blood from the peripheral tissues toward the heart. In this case, when a peripheral blood vessel is exposed to light emitted from a pixel, the light may be absorbed by the peripheral tissue. Absorbance is dependent on a hematocrit and a blood volume. The absorbance may have a maximum value during the systole of the heart and a minimum value during the diastole of the heart. Since the absorbance is in inverse proportion to an amount of light incident on the photo-sensor PS, absorbance at a corresponding point in time may be estimated through light reception data of the amount of light incident on the photo-sensor PS, and accordingly, as illustrated in FIG. 24, the light sensing data LSD over time may be generated.

The pulse wave information over time reflects the maximum value of the absorbance during the systole of the heart, and reflects the minimum value of the absorbance during the diastole of the heart. In addition, the pulse wave vibrates according to a heartbeat cycle. Accordingly, the pulse wave information may reflect a change in blood pressure according to a heartbeat.

Next, the main processor 800 generates the pulse wave signal PPG according to a pressure based on the pressure signal PSS and the light sensing data LSD (S300). The main processor 800 may generate a pulse wave signal PPG (see FIG. 26) having a value of the light sensing data LSD according to the pressure measurement value of the pressure signal PSS based on the received pressure signal PSS over time and light sensing data (LSD) over time.

Finally, the main processor 800 calculates a blood pressure based on the pulse wave signal PPG (S400). A method of calculating a blood pressure information based on the pulse wave signal PPG by the main processor 800 will be described later with reference to FIGS. 25 and 26.

Figure 25:
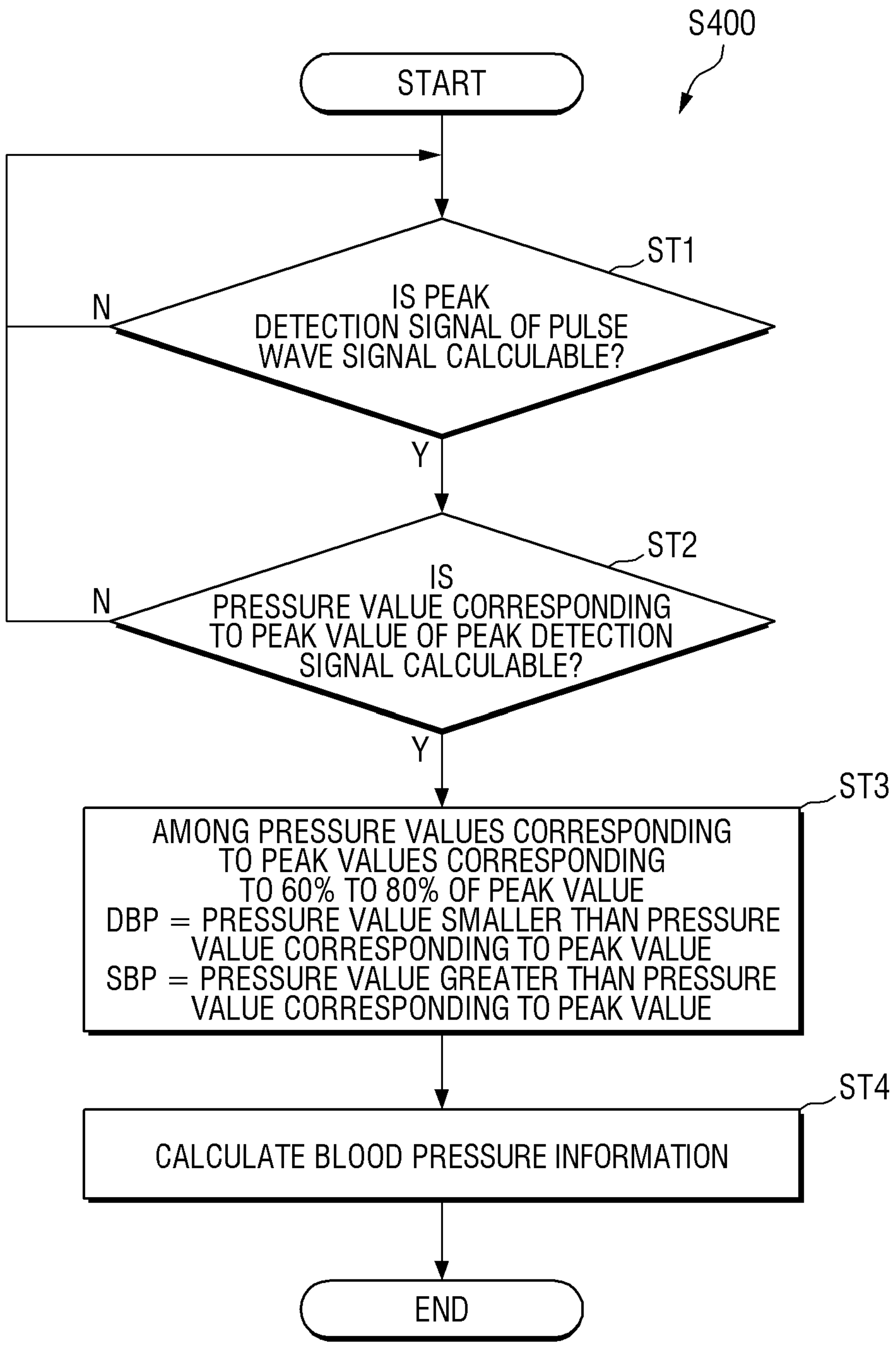
FIG. 25 is a flowchart illustrating a method of calculating a blood pressure according to an embodiment.
Figure 26:
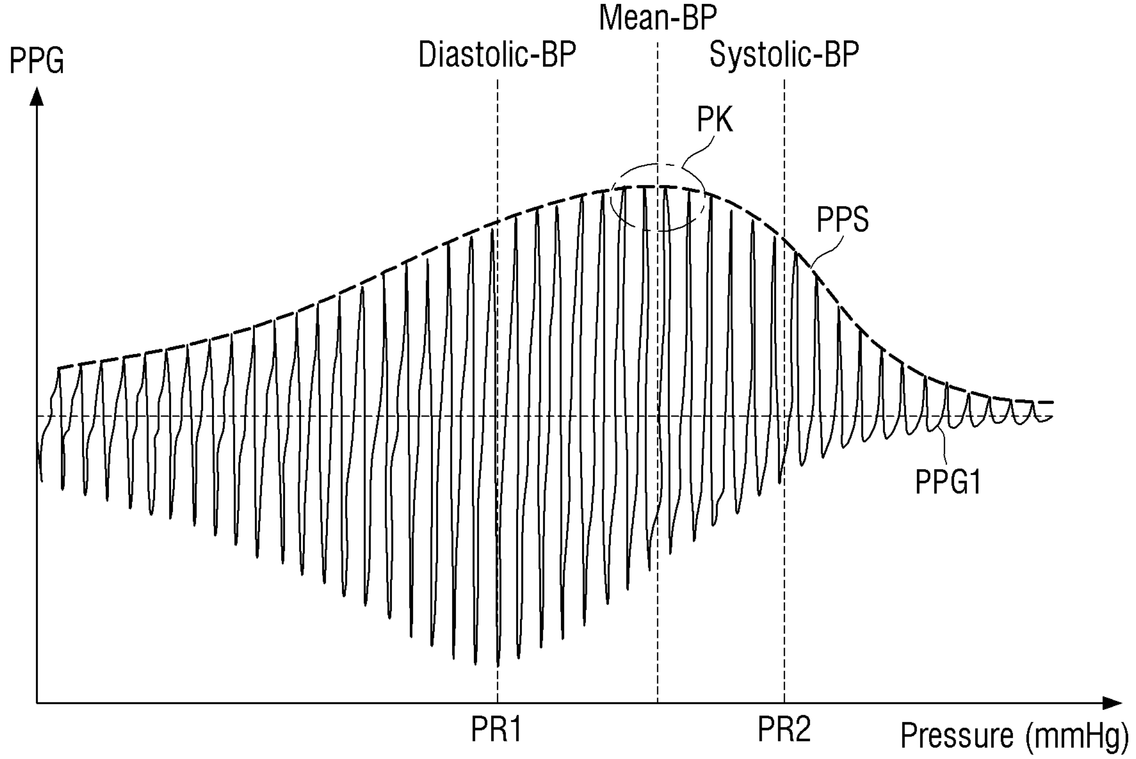
FIG. 26 is a graph illustrating a waveform of a peak detection signal.

FIG. 25 is a flowchart illustrating a method of calculating a blood pressure according to an embodiment. FIG. 26 is a graph illustrating a waveform of a peak detection signal.

Referring further to FIGS. 25 and 26, first, the main processor 800 decides whether or not a peak detection signal PPS may be calculated from the pulse wave signal PPG (ST1).

The main processor 800 may generate the peak detection signal PPS using peaks of the pulse wave signal PPG. The peak detection signal PPS is defined as a signal corresponding to each peak value of one cycle of the pulse wave signal PPG. For example, the pulse wave signal PPG may have one or more peak values. The main processor 800 may calculate the peak detection signal PPS including points corresponding to the peak values of the pulse wave signal PPG.

In this case, the peaks of the pulse wave signal PPG may correspond to peaks of the optical adjustment signal LCS. For example, each of the peaks of the pulse wave signal PPG may have the same value as the first amplitude V1 of the optical adjustment signal LCS. In addition, the first amplitude V1 of the M-th pressure section having the maximum value of the optical adjustment signal LCS may be a maximum value of the pulse wave signal PPG. For example, the incident light L1 emitted from the pixel PX of the display device 1 may be reflected as the pulse wave light L2 and L3 according to the first amplitude V1 of the optical adjustment signal LCS. Accordingly, the photo-sensor PS of the display device 1 senses the pulse wave light L2 and L3 to generate the light sensing data LSD. In addition, the main processor 800 of the display device 1 generates the pulse wave signal PPG based on the light sensing data LSD. For example, the peak of the pulse wave signal PPG may be generated according to the first amplitude V1 of the optical adjustment signal LCS.

Next, the main processor 800 decides whether or not a pressure value corresponding to the peak value PK of the peak detection signal PPS may be calculated (ST2). When a peak of the peak detection signal PPS exists, the main processor 800 may calculate a pressure value corresponding to the peak value PK of the peak detection signal PPS.

Next, the main processor 800 calculates a systolic blood pressure SBP, a diastolic blood pressure DBP, and the like, based on the peak value PK of the peak detection signal PPS (ST3), and calculates blood pressure information (ST4).

The main processor 800 may calculate the diastolic blood pressure DBP lower than the pressure value, the systolic blood pressure SBP higher than the pressure value, and a mean blood pressure according to the pressure value. For example, the main processor 800 may calculate pressure values corresponding to values corresponding to 60% to 80% of the peak value PK. The main processor 800 may calculate a pressure value that is smaller than a pressure value corresponding to the peak value PK among the pressure values as a first pressure value PR1. In addition, the main processor 800 may calculate the first pressure value PR1 as the diastolic blood pressure DBP. In addition, the main processor 800 may calculate a pressure value that is greater than the pressure value corresponding to the peak value PK among the pressure values as a second pressure value PR2. In addition, the main processor 800 may calculate the second pressure value PR2 as the systolic blood pressure SBP.

In a case of the embodiment, the pulse wave signal PPG vibrates according to the heartbeat cycle, and may thus reflect a change in blood pressure according to the heartbeat. The display device 1 may accurately calculate the blood pressure information based on the second feature point F2 and the amplitude V1 of the pulse wave signal PPG.

Figure 27:
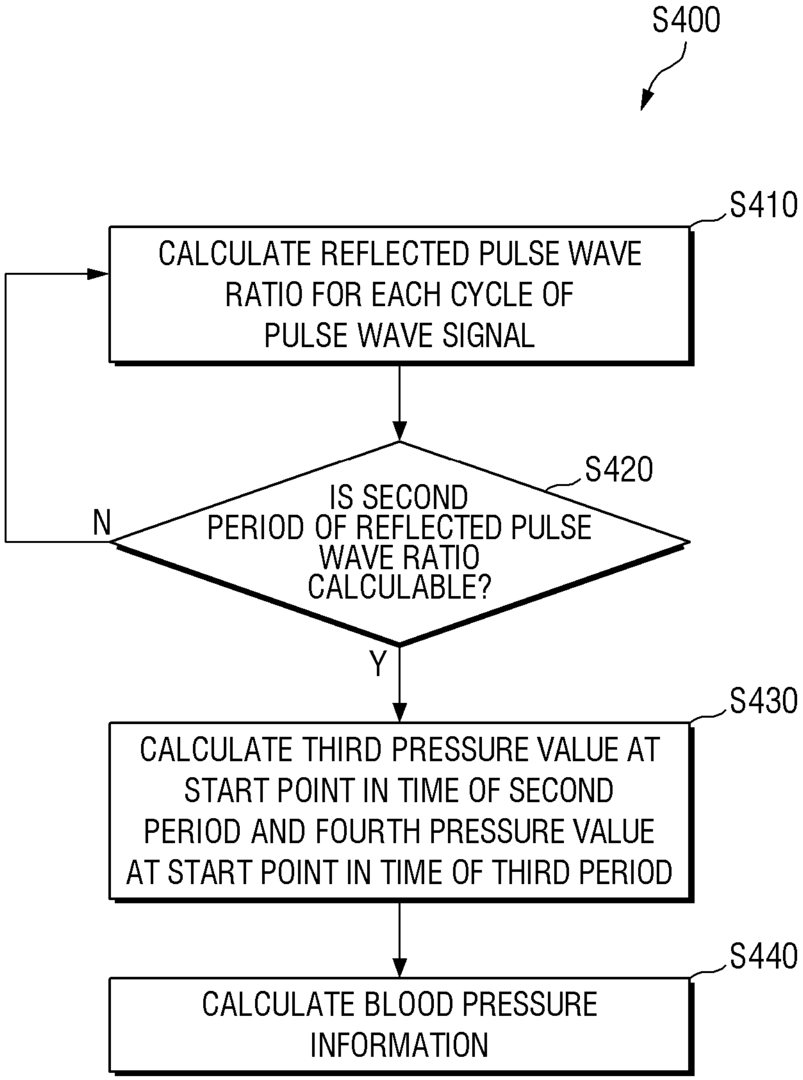
FIG. 27 is a flowchart illustrating a method of calculating a blood pressure by the display device according to an embodiment.
Figure 28:
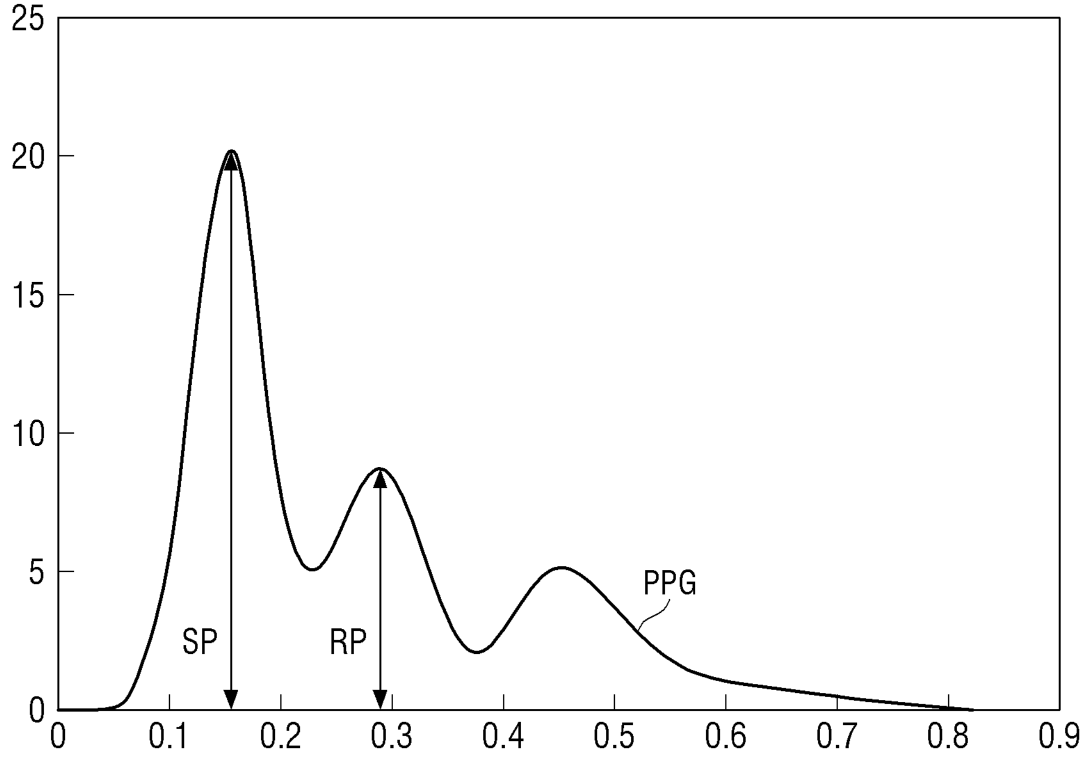
FIG. 28 is an enlarged graph of a waveform of one cycle of a pulse wave signal.
Figure 29:
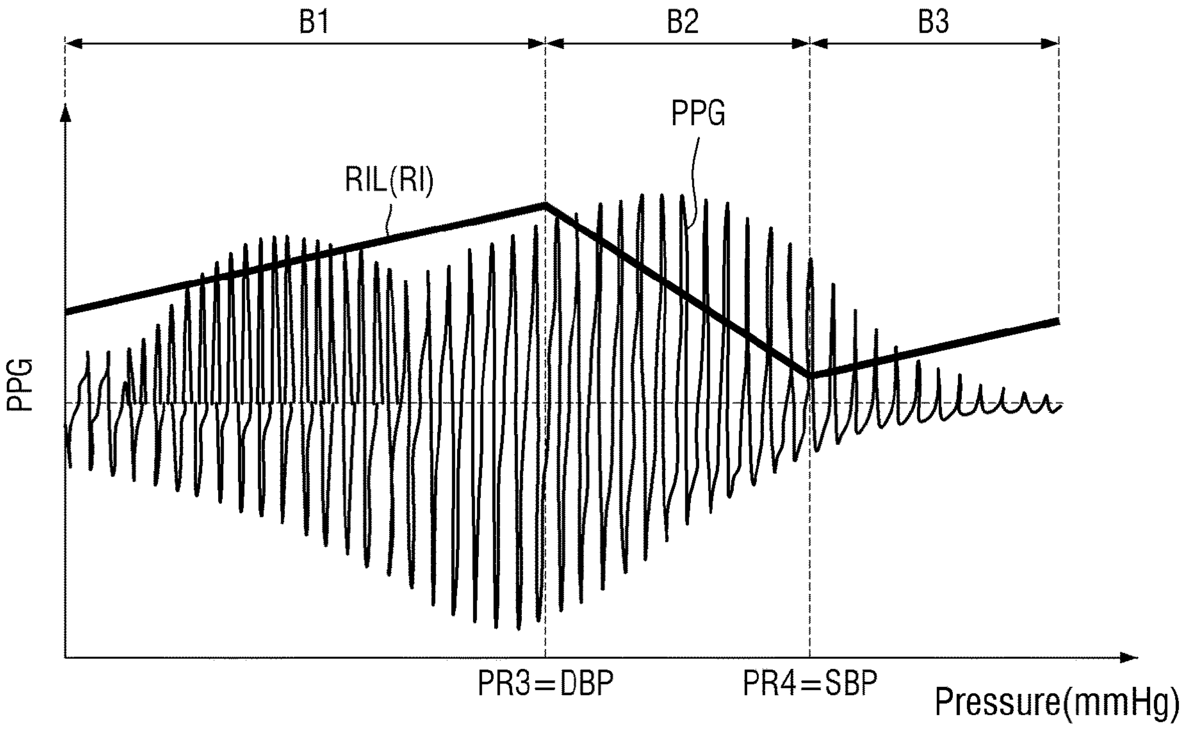
FIG. 29 is a graph illustrating a method of calculating a blood pressure using a generated pulse wave signal according to an embodiment.

FIG. 27 is a flowchart illustrating a method of calculating a blood pressure by the display device according to an embodiment. FIG. 28 is an enlarged graph of a waveform of one cycle of a pulse wave signal. FIG. 29 is a graph illustrating a method of calculating a blood pressure using a generated pulse wave signal according to an embodiment.

A method of calculating a blood pressure by the display device 1 will be described with reference to FIGS. 27 to 29. Referring to FIG. 27, first, a reflected pulse wave ratio RI is calculated for each cycle of the pulse wave signal PPG (S410).

Referring to FIG. 28, the main processor 800 may calculate the reflected pulse wave ratio RI of the pulse wave signal PPG. In order to calculate the reflected pulse wave ratio RI, the main processor 800 divides a wave cycle of the pulse wave signal PPG according to a period in which a wave according to a heartbeat and a reflected wave of a blood vessel are sequentially generated. For example, one cycle of the pulse wave signal PPG may include a plurality of waveforms having different amplitudes. Accordingly, when a peak value of a waveform having the greatest amplitude among the plurality of waveforms is defined as a pulse wave contraction value, a peak value of a waveform having the second greatest amplitude among the plurality of waveforms is defined as a reflected pulse wave value, the pulse wave contraction value is defined as Sp, the reflected pulse wave value is defined as RP, and the reflected pulse wave ratio is defined as RI, the reflected pulse wave ratio RI may be calculated by the following Equation 1.

$$RI = \frac{Rp}{Sp} \quad \text{[Equation 1]}$$

In this case, the pulse wave contraction value SP and the reflected pulse wave value RP may correspond to the first amplitude V1 and the second amplitude V2 of the optical adjustment signal LCS, respectively. For example, the pulse wave contraction value SP may correspond to the first amplitude V1 in an embodiment of FIGS. 15 to 18, and the reflected pulse wave value RP may correspond to the second amplitude V2. For example, the incident light L1 emitted from the pixel PX of the display device 1 may be reflected as the pulse wave light L2 and L3 according to the first amplitude V1 of the optical adjustment signal LCS. Accordingly, the photo-sensor PS of the display device 1 senses the pulse wave light L2 and L3 to generate the light sensing data LSD. In addition, the main processor 800 of the display device 1 generates the pulse wave signal PPG based on the light sensing data LSD. For example, the pulse wave contraction value SP and the reflected pulse wave value RP of the pulse wave signal PPG may be generated according to the first amplitude V1 and the second amplitude V2 of the optical adjustment signal LCS, respectively.

Second, the main processor 800 decides whether or not a second period B2 of the reflected pulse wave ratio RI may be calculated (S420). The main processor 800 sequentially stores detection results of reflected pulse wave ratios RI of reflected pulse waves to pulse wave contraction values, and analyzes the stored reflected pulse wave ratios RI. The main processor 800 may continuously change changes in magnitude of the reflected pulse wave ratios RI into data to analyze a change in magnitude of reflected pulse wave ratio data RIL(RI).

The reflected pulse wave ratio RI includes a first period B1 in which the reflected pulse wave ratio RI fluctuates within a first range, a second period B2 in which the reflected pulse wave ratio RI fluctuates within a second range, and a third period B3 in which the reflected pulse wave ratio RI fluctuates within a third range. For example, the main processor 800 may analyze a reflected pulse wave ratio signal RIL to analyze a first period B1 in which the reflected pulse wave ratio RI is gently changed within a preset range in a saturated state, a second period B2 in which the reflected pulse wave ratio RI is sharply decreased or increased in a preset range within a preset period, a third period B3 in which the reflected pulse wave ratio RI is gently changed within a preset range in a saturated state again after it is sharply decreased or increased, and the like.

Here, a width of the first range and a width of the third range may be smaller than a width of the second range. In addition, a gradient of the second period B2 of the reflected pulse wave ratio RI may be greater than a gradient of the first period B1 of the reflected pulse wave ratio RI and a gradient of the third period B3 of the reflected pulse wave ratio RI.

Finally, the main processor 800 calculates a systolic blood pressure SBP, a diastolic blood pressure DBP, and the like, based on the reflected pulse wave ratio RI (S430), and calculates blood pressure information (S440).

The main processor 800 may analyze the reflected pulse wave ratio RI to detect a start point in time of the second period B2. In addition, the main processor 800 may calculate a third pressure value PR3 corresponding to the pulse wave signal PPG at the start point in time of the second period B2. In addition, the main processor 800 may calculate the third pressure value PR3 as the diastolic blood pressure DBP. In addition, the main processor 800 may analyze the reflected pulse wave ratio RI to detect a start point in time of the third period B3 after the second period B2. In addition, the main processor 800 may calculate a fourth pressure value PR4 corresponding to the pulse wave signal PPG at the start point in time of the third period B3. In addition, the main processor 800 may calculate the fourth pressure value PR4 as the systolic blood pressure SBP.

Also in a case of the embodiment, the pulse wave signal PPG vibrates according to the heartbeat cycle, and may thus reflect a change in blood pressure according to the heartbeat. The display device 1 may accurately calculate the blood pressure information based on the reflected pulse wave ratio RI of the pulse wave signal PPG.

Accordingly, those skilled in the art will appreciate that many variations and modifications can be made to the described embodiments without substantially departing from the principles of the present disclosure.

What is claimed is:

1. A blood pressure calculation system, comprising:

a pulse wave generation apparatus configured to change a transmissivity of a first light provided thereto from an electronic display external to the blood pressure calculation system; and the electronic display configured to sense a first applied pressure, and configured to emit the first light, wherein the pulse wave generation apparatus includes:

a pressure sensor configured to sense a second applied pressure;

an optical adjustor configured to change a transmissivity of the first light;

a reflector configured to reflect the first light; and a controller configured to output, to the optical adjustor, an optical adjustment signal for changing the transmissivity based on a pressure measurement value received from the pressure sensor, and wherein the electronic display includes a photosensor, a display panel, and a main processor configured to control the display panel to emit the first light to the optical adjustor, configured to control the photo-sensor to sense a second light, which is a portion of the first light that is transmitted through the optical adjustor and reflected by the reflector to generate light sensing data, configured to generate a pulse wave signal based on the light sensing data and the sensed first applied pressure, and configured to analyze the pulse wave signal to calculate a blood pressure.

2. The blood pressure calculation system of claim 1, wherein the pressure measurement value is one of a plurality of pressure measurement values, and wherein the controller is configured to:

detect the plurality of pressure measurement values sensed by the pressure sensor as first to N-th pressure sections, and determine the optical adjustment signal based on the first to N-th pressure sections, wherein N is a positive integer.

3. The blood pressure calculation system of claim 2, wherein the optical adjustment signal has a waveform including a peak in each of the first to N-th pressure sections.

4. The blood pressure calculation system of claim 2, wherein the pressure sections include an M-th pressure section, where M is an integer greater than 1 and smaller than N, and wherein the controller is configured to calculate amplitudes of first to M-th optical adjustment signals so that the optical adjustment signal sequentially increases in the first to M-th pressure sections, and configured to calculate amplitudes of M-th to N-th optical adjustment signals so that the optical adjustment signal sequentially decreases in the M-th to N-th pressure sections.

5. The blood pressure calculation system of claim 4, wherein the main processor is configured to:

generate a peak detection signal based on peaks of the pulse wave signal and calculate a peak value of the peak detection signal and a pressure value corresponding to the peak value of the peak detection signal, and calculate a diastolic blood pressure lower than the pressure value, a systolic blood pressure higher than the pressure value, and a mean blood pressure according to the pressure value.

6. The blood pressure calculation system of claim 5, wherein the main processor is further configured to calculate the mean blood pressure as the pressure value corresponding to the peak value.

7. The blood pressure calculation system of claim 6, wherein the main processor is further configured to:

calculate a first pressure value that is smaller than the pressure value corresponding to 60% to 80% of the peak value in the peak detection signal and a second pressure value that is greater than the pressure value, and calculate the first pressure value as the diastolic blood pressure and calculates the second pressure value as the systolic blood pressure.

8. The blood pressure calculation system of claim 1, wherein the pressure measurement value is one of a plurality of pressure measurement values, and wherein the controller is configured to:

detect the plurality of pressure measurement values as first to N-th pressure sections, and determine the optical adjustment signal based on the first to N-th pressure sections, the determined optical adjustment signal including a plurality of waveforms, each of the plurality of waveforms having a different amplitude.

9. The blood pressure calculation system of claim 8, wherein a first amplitude of a first waveform of the plurality of waveforms is greater than a second amplitude of a second waveform of the plurality of waveforms.

10. The blood pressure calculation system of claim 9, wherein the pulse wave signal includes a plurality of waveforms having different amplitudes, and wherein the main processor is configured to calculate a reflected pulse wave ratio RI according to the formula:

$$RI = \frac{Rp}{Sp}$$

in which SP is a pulse wave contraction value, RP is a reflected pulse wave value, the pulse wave contraction value is an amplitude of a first waveform of the plurality of waveforms, and the reflected pulse wave value is an amplitude of a second waveform of the plurality of waveforms of the pulse wave signal.

11. The blood pressure calculation system of claim 10, wherein the reflected pulse wave ratio is the same as a ratio between the first amplitude and the second amplitude.

* * * * *